United States Patent
Zuckermann et al.

(10) Patent No.: US 6,569,450 B1
(45) Date of Patent: May 27, 2003

(54) LIPID-CONJUGATED POLYAMIDE COMPOUNDS AND RELATED COMPOSITIONS AND METHODS THEREOF

(75) Inventors: Ronald N. Zuckermann, Berkeley, CA (US); Chin-Yi Huang, Fremont, CA (US); John E. Murphy, Oakland, CA (US); Tetsuo Uno, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/620,260

(22) Filed: Jul. 21, 2000

Related U.S. Application Data

(62) Division of application No. 09/132,808, filed on Aug. 12, 1998, now Pat. No. 6,197,332.
(60) Provisional application No. 60/054,743, filed on Aug. 13, 1997.

(51) Int. Cl.[7] .................. A61K 9/127; C08K 5/20; C12N 15/00; C07C 231/00
(52) U.S. Cl. .................. 424/450; 552/502; 552/544; 524/728; 554/35; 554/36; 554/37; 554/79; 935/52; 935/54
(58) Field of Search ................ 424/450, 1.21, 424/9.321, 9.51, 94.3; 552/502, 544; 554/35, 36, 37, 79; 524/728; 435/52, 54

(56) References Cited

U.S. PATENT DOCUMENTS

| | | |
|---|---|---|
| 5,334,761 A | 8/1994 | Gebeyehu et al. |
| 5,395,619 A | 3/1995 | Zalipsky et al. |
| 5,534,259 A | 7/1996 | Zalipsky et al. |
| 5,595,756 A | 1/1997 | Bally et al. |
| 5,635,487 A | 6/1997 | Wolff et al. |
| 5,679,559 A | 10/1997 | Kim et al. |
| 5,705,385 A | 1/1998 | Bally et al. |

FOREIGN PATENT DOCUMENTS

| | | |
|---|---|---|
| EP | 545 016 A1 | 9/1992 |
| EP | 544 292 A3 | 6/1993 |
| WO | WO 91/19735 | 12/1991 |
| WO | WO 93/14778 | 8/1993 |
| WO | WO 94/06451 | 3/1994 |
| WO | WO 95/02397 | 1/1995 |
| WO | WO 95/28494 | 10/1995 |
| WO | WO 95/31557 | 11/1995 |
| WO | WO 96/04001 | 2/1996 |
| WO | WO 96/18372 | 6/1996 |
| WO | WO 96/22765 | 8/1996 |
| WO | WO 96/27379 | 9/1996 |
| WO | WO 97/11682 | 4/1997 |
| WO | WO 97/12052 | 4/1997 |
| WO | WO 97/45442 | 12/1997 |
| WO | WO 98/06437 | 2/1998 |
| WO | WO 98/27209 | 6/1998 |

OTHER PUBLICATIONS

Aberle, A.M., et al., "A Novel Tetraester Construct that Reduces Cationic Lipid–Associated Cytotoxicity Implications for te Onset of Cytotoxicity" *Biochemistry* 37:6533–6540 (1998).

(List continued on next page.)

*Primary Examiner*—Gollamudi S. Kishore
(74) *Attorney, Agent, or Firm*—LeeAnn Gorthey; Steven W. Collier; Robert P. Blackburn

(57) ABSTRACT

In accordance with the present invention, there are provided lipid-conjugated polyamide compounds and related compositions and methods thereof. Lipid-conjugated polyamide compounds of the present invention are particularly useful as vehicles for delivering biologically active agents to a target site. In particular, the invention compounds are effective at facilitating the delivery of polynucleotides to cells. The present invention also provides a method for producing stable formulations of polynucleotides complexed with a delivery vehicle.

16 Claims, 15 Drawing Sheets

OTHER PUBLICATIONS

Batra, R.K., et al., "Receptor–Mediated Gene Delivery Employing Lectin–Binding Specificity" *Gene Therapy* 1:255–260 (1994).

Behr, J.P., et al., "Gene Transfer With Synthetic Cationic Amphiphiles: Prospects for Gene Therapy" *Bioconjugate Chem.* 5:382–389 (1994).

Behr, J.P., et al., "The Proton Sponge: A Trick to Enter Cells the Viruses did not Exploit" *Chimia* 51:34–36 (1997).

Crook, K., et al., "Inclusion of Cholesterol in DOTAP Transfection Complexes Increases the Delivery of DNA to Cells in Vitro in the Presence of Serum" *Gene Therapy* 5:137–143 (1998).

Gao, X. and Huang, L., "Cationic Liposome–Mediated Gene Transfer" *Gene Therapy* 2:710–722 (1995).

Gao, X. and Huang, L., "Potentiation of Cationic Liposome–Mediated Gene Transfer Delivery by Polycations" *Biochemistry* 35:1027–1036 (1996).

Guy, J., et al., "Delivery of DNA into Mammalian Cells by Receptor–Mediated Endocytosis and Gene Therapy" *Molecular Biotechnology* 3:237–248 (1995).

Hong, K., et al., "Stabilization of Cationic Liposome–Plasmid DNA Complexes by Polyamines and Poly(ethylene glycol)–phospholipid Conjugates for Efficient in vivo Gene Delivery" *FEBS Letters* 400:233–237 (1997).

Kabanov, A.V. and Kabanov, V.A., "DNA Complexes with Polycations for the Delivery of Genetic Material into Cells" *Bioconjugate Chem.* 6:7–20 (1995).

Lasic, D.D. and Templeton, N.S., "Liposomes in Gene Therapy" *Advanced Drug Delivery Reviews* 20:221–226 (1996).

Ledley, F.D., "Nonviral gene therapy: the promise of genes as pharmaceutical products" *Human Gene Ther.* 6:1129–1144 (1995).

Legendre, J.Y., et al., "Dioleoylmelittin as a Novel Serum–Insensitive Reagent for Efficient Transfection of Mammalian Cells" *Bioconjugate Chem.* 8:57–63 (1997).

Liu, Y., et al., "Cationic Liposome–Mediated Intravenous Gene Delivery" *J. Biological Chemistry* 270(42):24864–24870 (1995).

Mastrangelo, M.J., et al., "Gene therapy for human cancer: an essay for clinicians" *Seminars in Oncology* 23(1):4–21 (1996).

Merwin, J.R., et al., "Targeted Delivery of DNA Using YEE(GalNAcAH)$_3$, a Synthetic Glycopeptide Ligand for the Asialoglycoprotein Receptor" *Bioconjugate Chemistry* 5(6):612–620 (1994).

Michael, S.I. and Curiel, D.T., "Strategies to Achieve Targeted Gene Delivery via the Receptor–Mediated Endocytosis Pathway" *Gene Therapy* 1:223–232 (1994).

Ngo, et al., "Computational Complexity, Protein Structure Prediction, and the Levinthal Paradox" *The Protein Folding Problem and Tertiary Structure Prediction,* Mertz et al. (eds.) Birkhauser, Boston MA pp. 433 and 492–495 (1994).

Phillips, S.C., "Receptor–Mediated DNA Delivery Approaches to Human Gene Therapy" *Biologicals* 23:13–16 (1995).

Remy, J.S., et al., "Targeted Gene Transfer into Hepatoma Cells With Lipopolyamine–Condensed DNA Particles Presenting Galactose Ligands: a Stage Toward Artificial Viruses" *Proc. Natl. Acad. Sci. USA* 92:1744–1748 (1995).

Richter, L.S. and Zuckermann, R.N., "Synthesis of Peptide Nucleic Acids (PNA) by Submonomer Solid–Phase Synthesis" *Bioorganic and Medicinal Chemistry Letters* 5(11):1159–1162 (1995).

Tomlinson, E. and Rolland, A., "Controllable Gene Therapy Pharmaceutics of Non–Viral Gene Delivery Systems" *J. Controlled Release* 39:357–372 (1996).

Wagner, E., et al., "DNA–Binding Transferrin Conjugates as Functional Gene–Delivery Agents: Synthesis by Linkage of Polylysine or Ethidium Homodimer to the Transferrin Carbohydrate moiety" *Bioconjugate Chem.* 2(4):226–231 (1991).

Wagner, E., et al., "Influenza Virus Hemagglutinin HA–2 N–terminal Fusogenic Peptides Augment Gene Transfer by Transferrin–Polylysine–DNA Complexes: Toward a Synthetic Virus–Like Gene–Transfer Vehicle" *Proc. Natl. Acad. Sci. USA* 89:7934–7938 (1992).

Wheeler, C.J., et al., "Converting an alcohol to an amine in a cationic lipid dramatically alters the co–lipid requirement, cellular transfection activity and the ultrastructure of DNA–cytofectin complexes" *Biochim. et Biophsica Acta* 1280 1–11 (1996).

Yagi, Y., et al., "Interaction of poly N–(3–aminopropyl)glycine! and its derivatives with lipid membrane" *Bull Chem Soc Jpn* 61(11):3983–3989 (1988).

Zhou, X., et al., "DNA Trasnfecion Mediated by Cationic Liposomes Containing Lipopolylysine: Characterization and Mechanism of Action" *Biochimica et Biophysica Acta* 1189:195–203 (1994).

Stept 1: Acylation
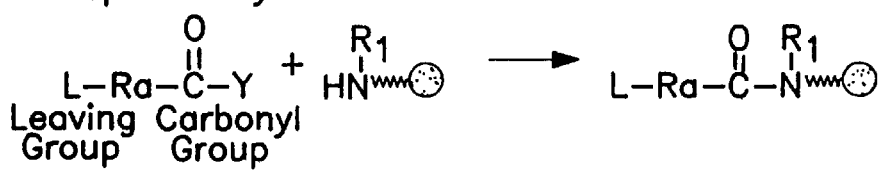
Step 2: Nucleophilic Displacement
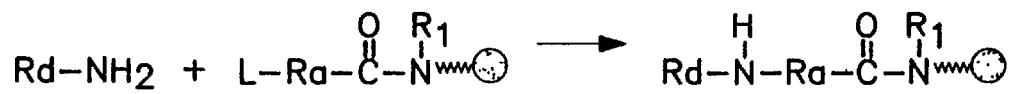
FIG. I

LIPID-CONJUGATED POLYAMIDE COMPOUNDS AND RELATED COMPOSITIONS AND METHODS THEREOF

This application claims the benefit of U.S. Provisional Application is a divisional of U.S Ser. No. 09/132,808 now U.S. Pat. No. 6,197,332, filed Aug. 12, 1998, which No. 60/054,734, filed Aug. 13, 1997, both of which are incorporated herein by reference.

FIELD OF THE INVENTION

The present invention relates to lipid-conjugated polyamide compounds, methods for making them, as well as compositions and methods for their use, such as, for example, in the delivery of biologically active agents to cells.

BACKGROUND OF THE INVENTION

The discovery of new therapeutic agents having increasingly complex molecular structure has presented new challenges related to how they can be efficiently delivered to targeted sites. For example, recent developments in recombinant DNA technology and human genome characterization have enabled identification of the moleculer origins of many genetic and acquired diseases and construction of appropriate plasmids containing desired genes. However, the efficient delivery of these large and heavily charged constructs, having molecular weights of up to tens of millions of daltons and containing several tens of thousands of negative charges into cells remains a substantial challenge. Studies evaluating the use of neutral and cationic liposome structures as vehicles for the delivery of polynucleotides to cells have met with limited success, as these encapsulated structures are rather large and unstable.

Accordingly, compounds that can be used as effective vehicles for the efficient delivery of large complex agents, such as polynucleotides, to cells would be highly desirable.

SUMMARY OF THE INVENTION

The present invention is directed to lipid-conjugated polyamide compounds and compositions thereof that are particularly useful in the delivery of bioactive agents to cells.

Specifically, the present invention provides lipid-conjugated polyamide compounds having the general formula:

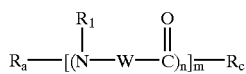
(I)

wherein n is an integer selected from 1 to about 48 and m is an integer selected from about 2 to about 48,

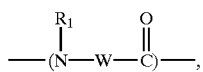

wherein $R_1$ for each monomeric unit, and $R_a$ are independently selected from the group consisting of a hydrogen atom; a hydroxy group; an amino group; a carboxyl group; a sulfonyl group; -SH; an optionally substituted, branched or straight chain aliphatic group having from about 1 to about 8 carbon atoms in a backbone structure that optionally contains nitrogen, oxygen, sulfur, and phosphorus, wherein said aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl component of said arylalkyl optionally has one or more double or triple bonds; and a lipid moiety that is optionally bonded to a linker moiety, wherein $R_1$ is not a hydrogen atom for at least one monomeric unit, wherein $R_c$ is selected from a hydrogen atom; a hydroxy group; an amino group; a hydrazine group; a sulfonyl group; —SH; an optionally substituted, branched or straight chain aliphatic group having from 1 to about 8 carbon atoms in a backbone structure that optionally contains nitrogen, oxygen, sulfur, and phosphorus, wherein said aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein when $R_1$, $R_a$, or $R_c$ is an aryl or arylalkyl group having fewer than about 5 carbon atoms in a backbone structure, said backbone structure further comprises one or more heteroatoms, wherein W for each monomeric unit is independently selected from an optionally substituted, branched or straight chain divalent moiety having from 1 to about 50 atoms and optionally, one or more double or triple bonds in a backbone that contains carbon and optionally contains nitrogen, oxygen, sulfur, and phosphorus, wherein said optional substitution of W may be a lipid moiety that is optionally bonded to a linker moiety, wherein said lipid moiety is a hydrophobic or amphipathic moiety selected from the group consisting of:

(i) optionally substituted aryl or arylalkyl moieties having from about 14 to about 50 carbon atoms in a backbone structure that optionally contains nitrogen, oxygen, sulfur, and phosphorus, wherein the alkyl component of said arylalkyl optionally has one or more double or triple bonds; and (ii) optionally substituted, branched or straight chain aliphatic moieties having from about 10 to about 50 carbon atoms in a backbone structure that optionally contains nitrogen, oxygen, sulfur, and phosphorus, wherein said aliphatic moieties optionally have one or more double or triple bonds, and wherein at least one of $R_a$, $R_c$, W for a single monomeric unit and $R_1$ for a single monomeric unit comprises a lipid moiety optionally bonded to a linker moiety.

The present invention also provides a method of synthesizing lipid-conjugated polyamide compounds, said method comprising:

a) contacting
(1) a lipid reactant, with
(2) an oligomer reactant, wherein said oligomer reactant has the general formula:

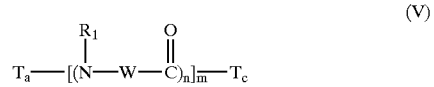

(V)

wherein n is an integer selected from 1 to about 48, and m is an integer from about 2 to about 48, wherein each $T_a$ and $T_c$ is independently selected from a terminal group and a reactive moiety that is capable of further reaction with said lipid reactant, wherein $R_1$ for each monomeric unit,

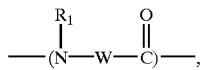

in said oligomer reactant is selected from the group consisting of a hydrogen atom; a hydroxy group; an amino group; a carboxyl group; a sulfonyl group, —SH; an optionally substituted, branched or straight chain aliphatic group having from 1 to about 8 carbon atoms in a backbone structure that optionally contains nitrogen, oxygen, sulfur, and phosphorus, wherein the aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl group of said arylalkyl optionally has one or more double or triple bonds; and a reactive moiety that is capable of further reaction with said lipid reactant, wherein when $R_1$, $R_a$, or $R_c$, is an aryl or arylalkyl group having fewer than about 5 carbon atoms in a backbone structure, said backbone structure further comprises one or more heteroatoms, wherein $R_1$ is not a hydrogen atom for at least one monomeric unit, wherein W for each monomeric unit is selected from an optionally substituted, branched or straight chain divalent moiety having from 1 to about 50 atoms in a backbone that contains carbon, and optionally contains nitrogen, oxygen, sulfur, and phosphorus, and optionally one or more double or triple bonds, wherein said optional substitution of W may be a reactive moiety that is capable of further reaction with said lipid reactant, wherein at least one of $T_a$, $T_c$, W for a single monomeric unit, or $R_1$ for a single monomeric unit comprises a reactive moiety that is capable of further reaction with said lipid reactant; then b) reacting said lipid reactant with said oligomer reactant to conjugate the lipid reactant to the oligomer reactant.

In another embodiment, the present invention provides a composition comprising a lipid-conjugated polyamide compound of the present invention and a biologically active agent.

In yet another embodiment, the present invention provides a method for inducing the uptake of a biologically active agent by a cell, said method comprising:

providing a composition comprising an effective amount of a biologically active agent and a lipid-conjugated polyamide compound of the present invention; then contacting a biological sample with an effective dose of said composition, wherein said biological sample comprises a cell.

In still another embodiment, the present invention provides a method for inducing the uptake of a biologically active agent by a cell in vivo, said method comprising:

providing a composition comprising an effective amount of a biologically active agent and a lipid-conjugated polyamide compound of the present invention; then administering an effective dose of said composition to a subject.

In a further embodiment, the present invention provides a method of expressing a gene in a mammal, said method comprising:

administering a polynucleic acid complexed with a lipid-conjugated polyamide compound of the present invention to a mammal, wherein said polynucleic acid is capable of functionally expressing said gene in said mammal, and wherein said complex is effective at transfecting said gene into a cell in said mammal.

In another embodiment, the present invention provides a method for substantially inhibiting nuclease-induced polynucleotide degradation, said method comprising:

contacting a polynucleotide with a degradation-inhibiting quantity of a lipid-conjugated polyamide compound, and introducing the polynucleotide and the lipid-conjugated polyamide compound into a nuclease-containing environment.

In still a further embodiment, the present invention provides a method of making a stable preparation of a polynucleic acid complexed with a delivery vehicle, said method comprising:

a) providing a polynucleic acid in a first liquid carrier as a dilute polynucleic acid solution that is substantially precipitant-free;

b) providing a delivery vehicle-forming compound in a second liquid carrier as a delivery vehicle solution that is substantially precipitant-free;

c) combining said dilute polynucleic acid solution with said delivery vehicle solution to form a dilute preparation of delivery vehicle/polynucleic acid complex; then d) reducing the volume of said dilute preparation to form a stable preparation of delivery vehicle/polynucleic acid complex, wherein the concentration of polynucleic acid in said stable preparation is higher than the concentration of polynucleic acid in said dilute polynucleic acid solution, and wherein said stable preparation is substantially precipitant-free.

BRIEF DESCRIPTION OF THE DRAWINGS

FIG. 1 shows a reaction scheme for preparing lipid-conjugated polyamide compounds.

Luciferase activity in transfected cells is shown on the y-axis in (pg/20 µl) and the +/− charge ratio is shown on the x-axis. The open bars refer to cells grown in FCS-supplemented medium and the shaded bars refer to cells grown in Opti-MEM (i.e., serum-free medium).

Figure 4:
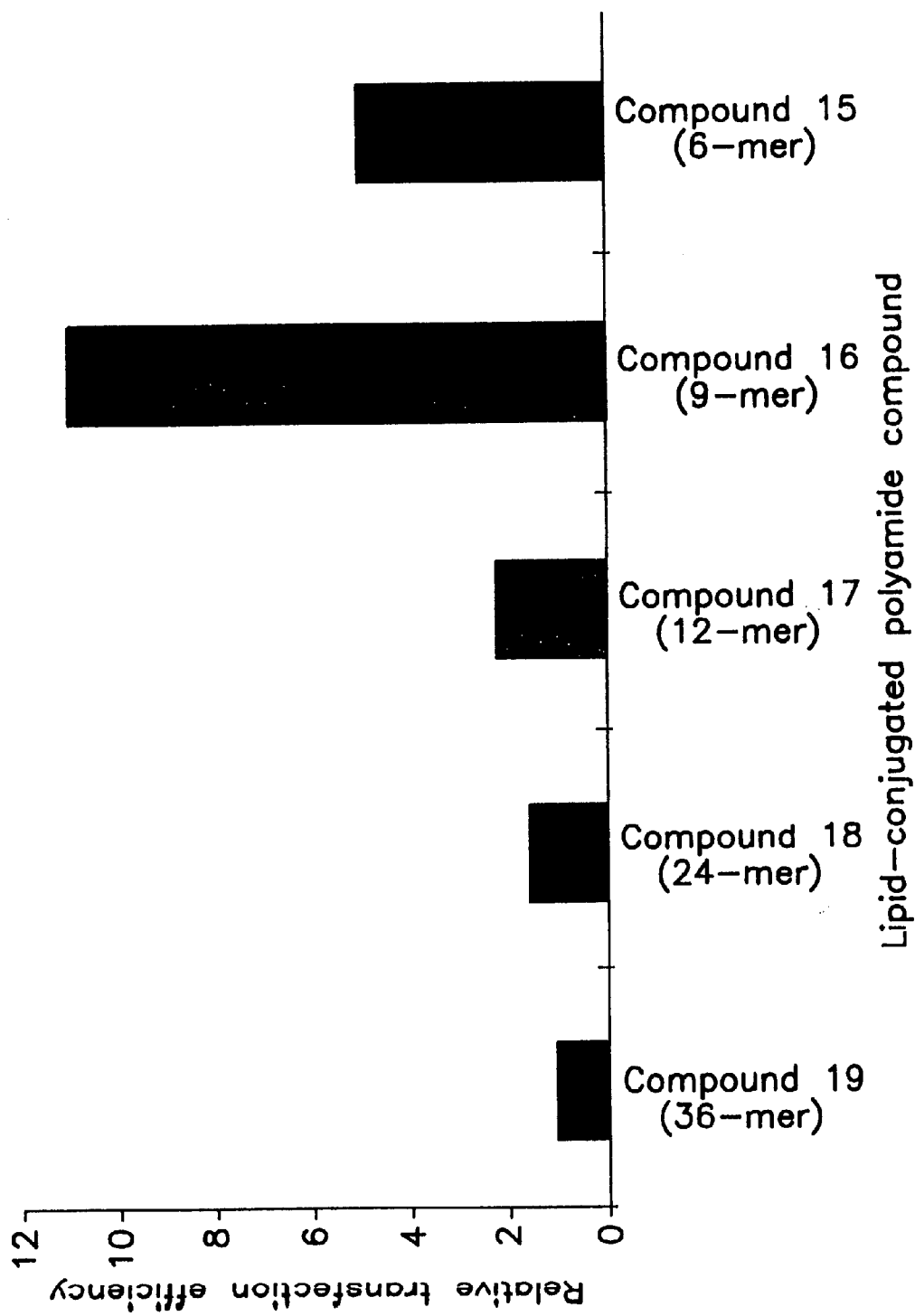

FIG. 4 shows the relationship between transfection efficiency and total number of monomeric units in the oligomeric moiety of lipid-conjugated polyamide compounds of the present invention. Luciferase activity (all normalized to luciferase activity corresponding to the 36-mer (i.e., n=3, m=12 with reference to formula (I))) in transfected HT1080 cells is shown on the y-axis and length of oligomer is shown on the x-axis. The lipid-conjugated polyamide/DNA complexes had a +/− charge ratio of 2:1.

Figure 5:
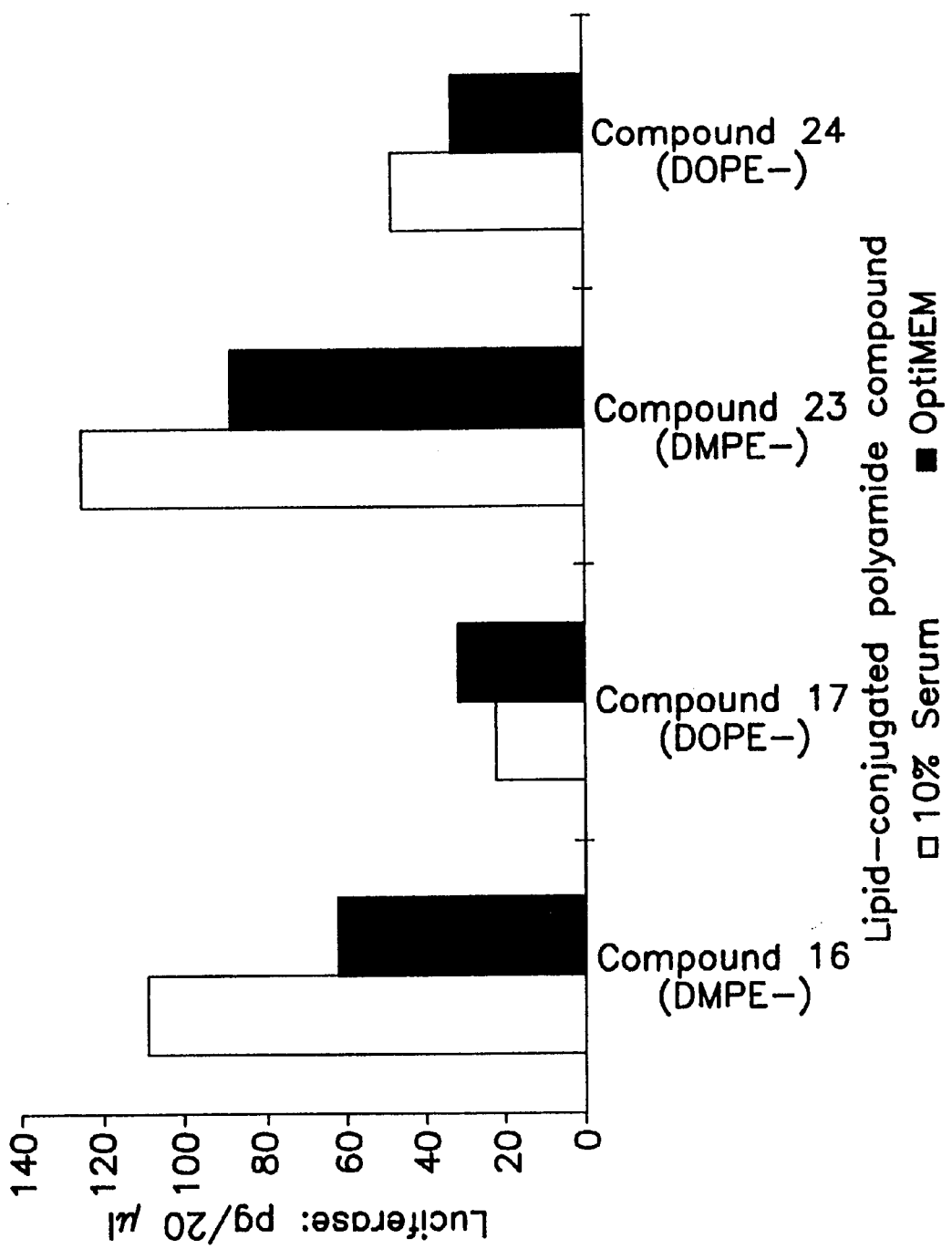

FIG. 5 shows a comparison in transfection efficiency between DMPE-conjugated polyamide compounds (i.e., Compounds 16 and 23) and DOPE-conjugated polyamide compounds (i.e., Compounds 20 and 24). The open bars refer to cells grown in FCS-supplemented medium and the shaded bars refer to cells cultured in optiMEM (i.e., serum-free medium).

Figure 6:
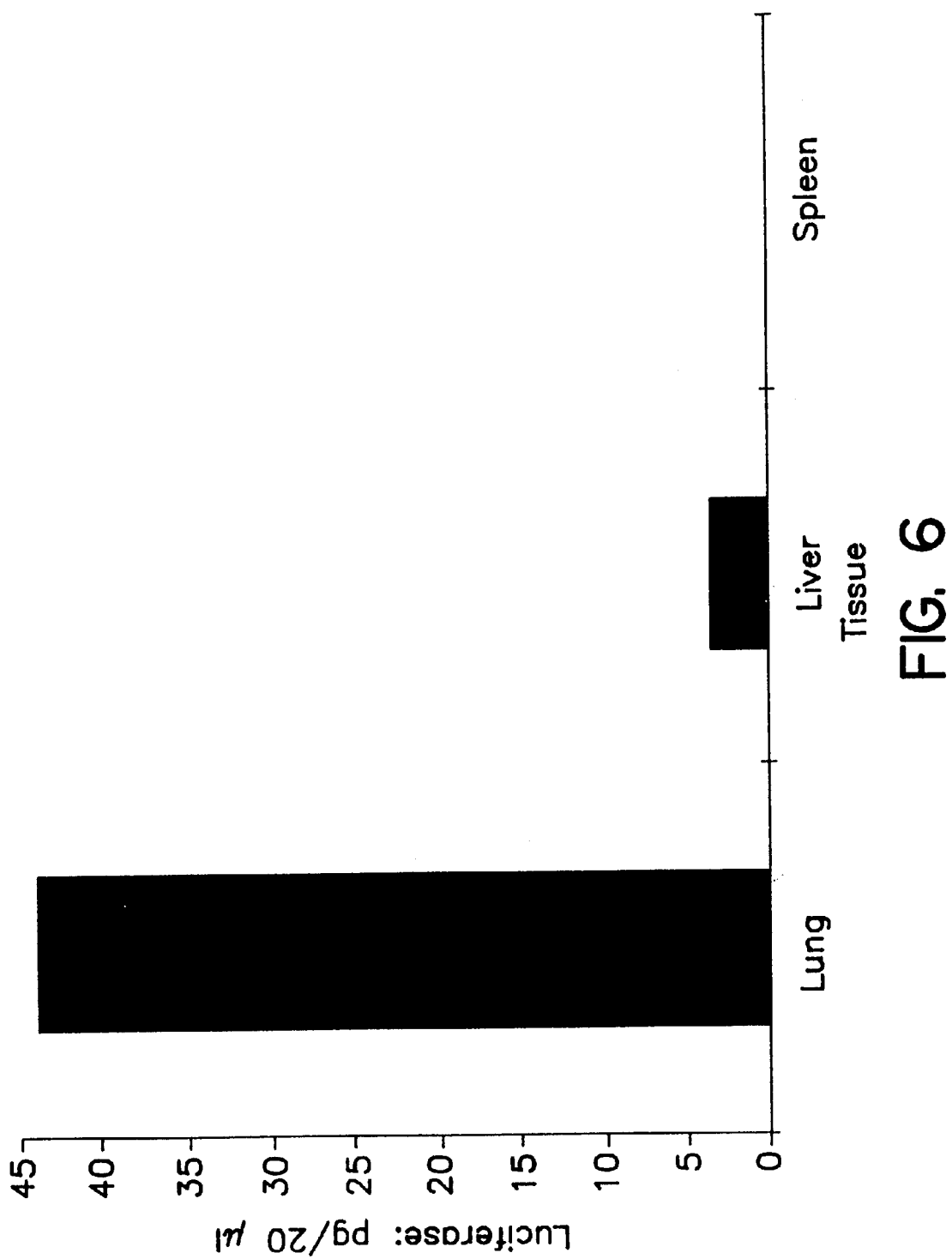

FIG. 6 shows luciferase expression in Balb/C mouse lung, liver, and spleen tissue after in vivo transfection with lipid-conjugated polyamide compound (Compound 16)/pCMVkmLUC complex.

Figure 7:
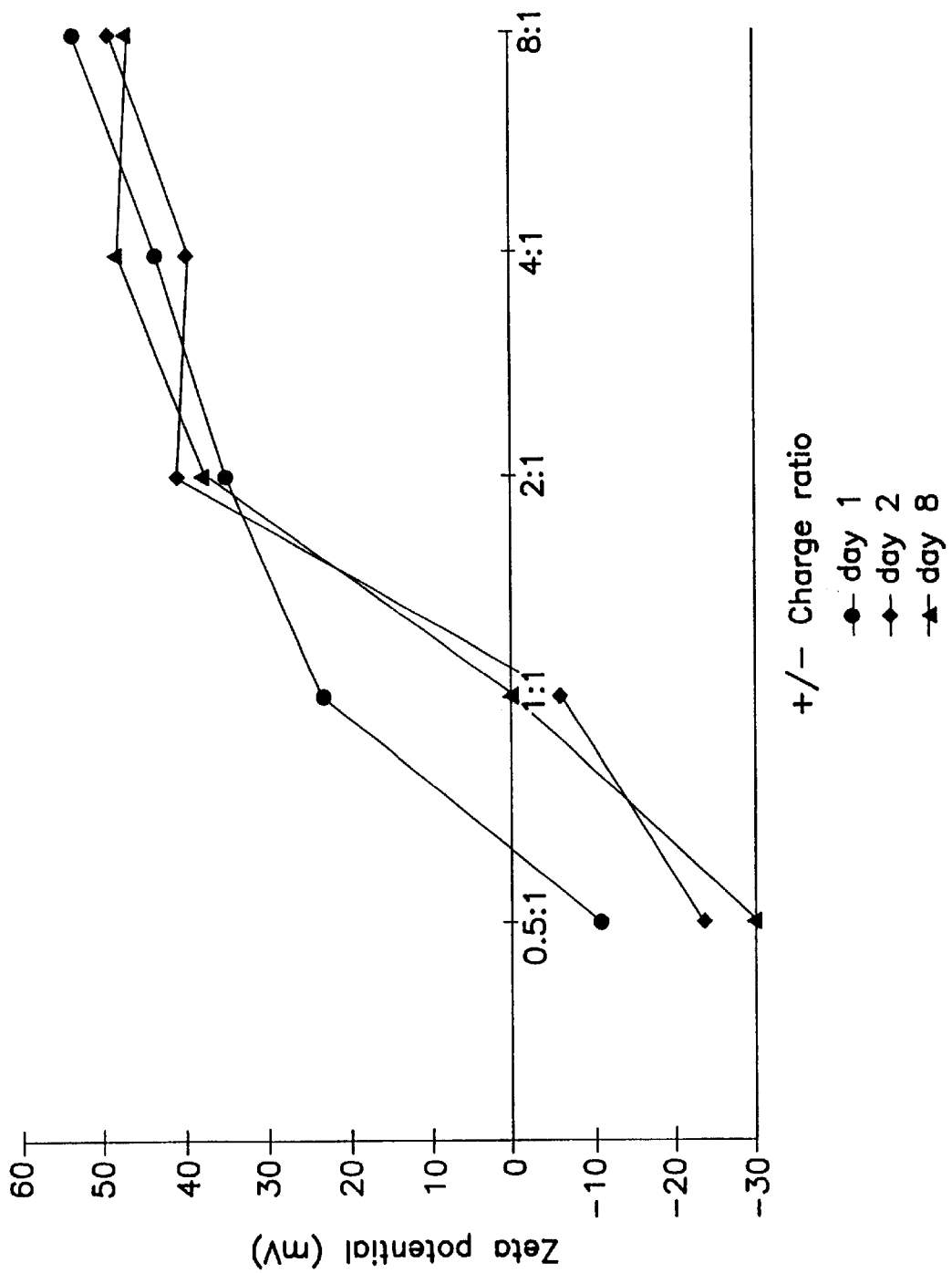

FIG. 7 shows zeta potential stability over a period of 8 days of a formulation of lipid-conjugated polyamide (Compound 16)/DNA complex, prepared by the "dilution-concentration" formulation method of the present invention.

Figure 8:
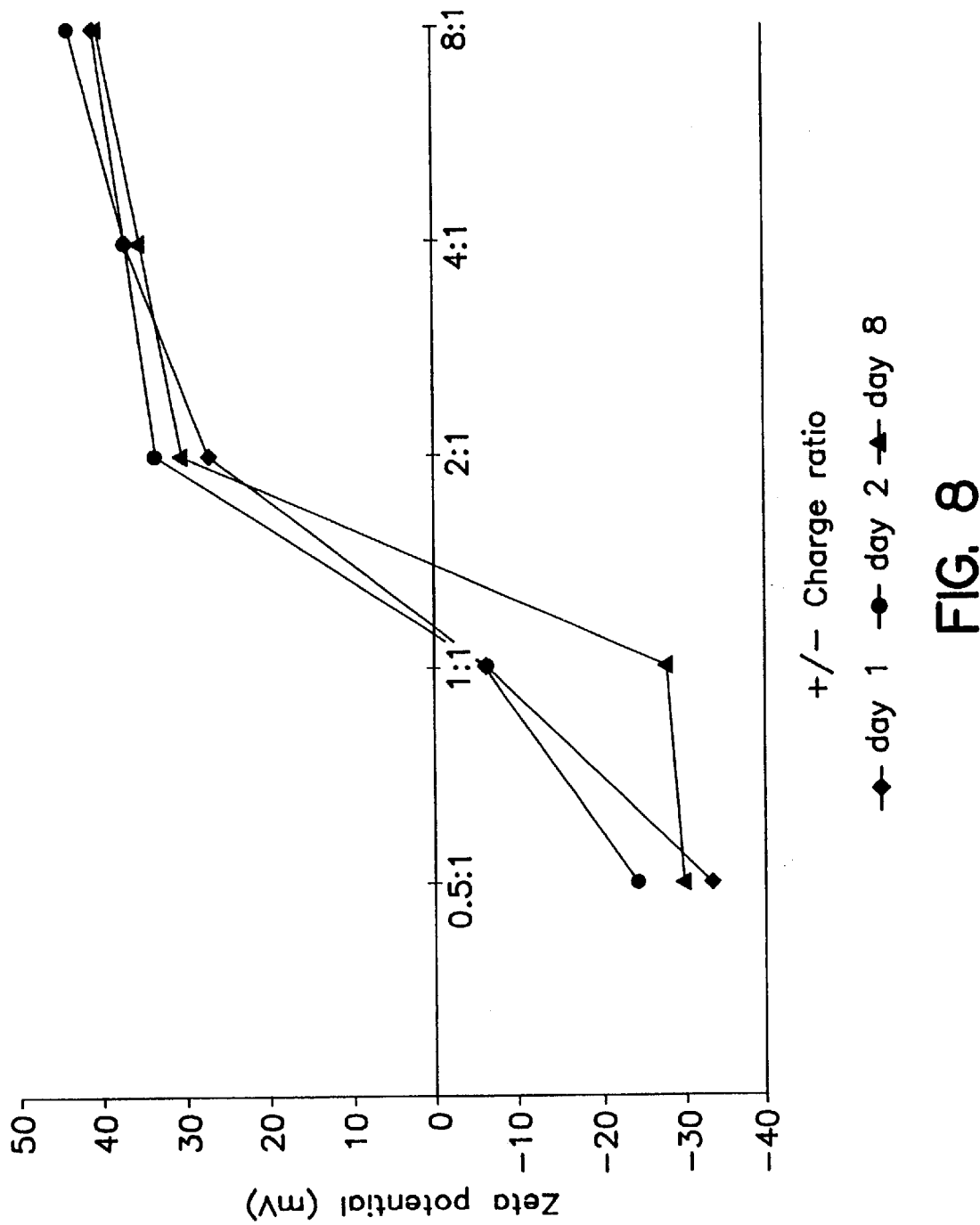

FIG. 8 shows zeta potential stability over a period of 8 days of a formulation of lipid-conjugated polyamide (Compound 23)/DNA complex, prepared by the "dilution-concentration" formulation method.

Figure 9:
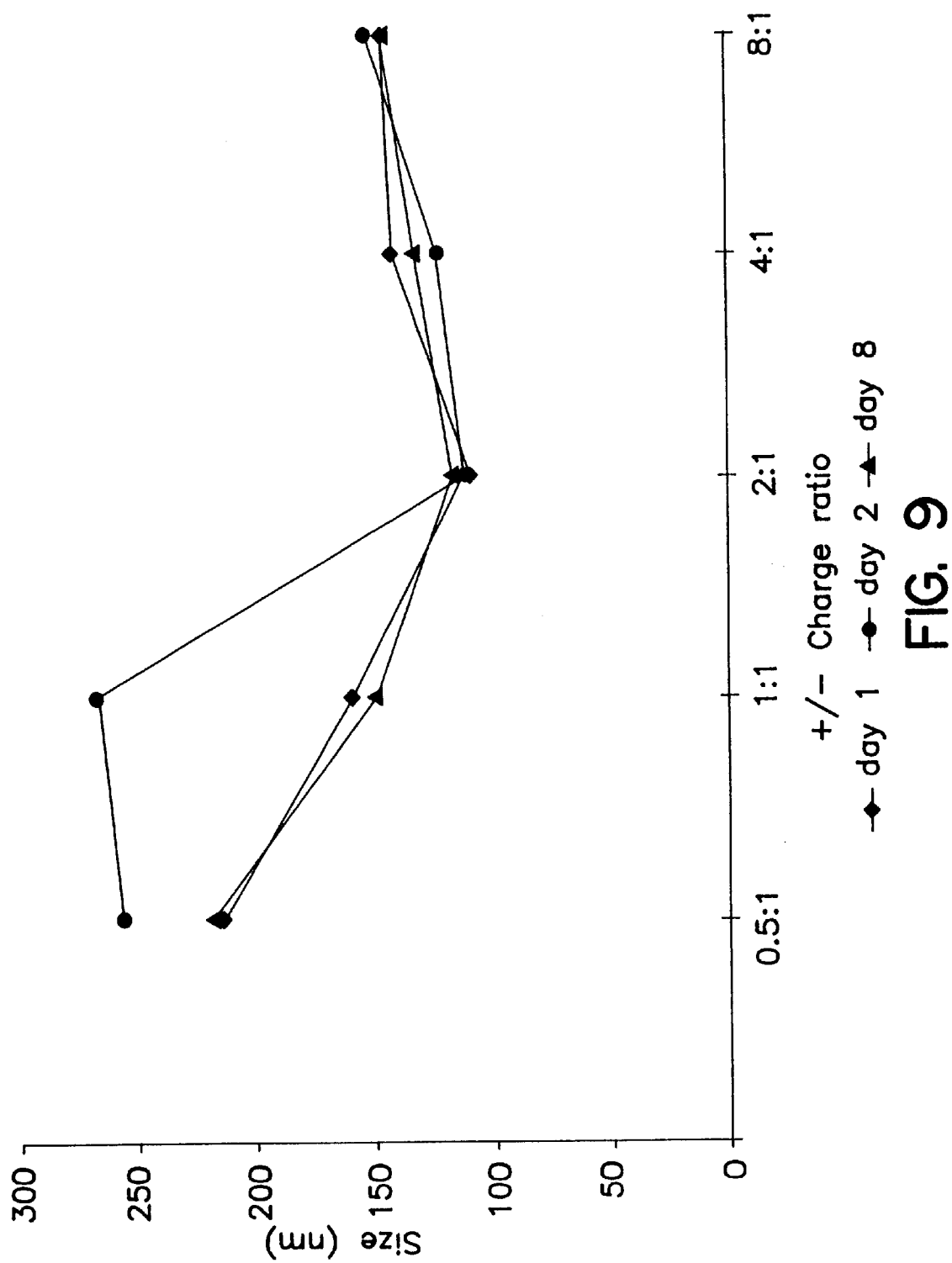

FIG. 9 shows particle size stability over a period of 8 days of a formulation of lipid-conjugated polyamide (Compound 16)/DNA complex, prepared by the "dilution-concentration" formulation method.

Figure 10:
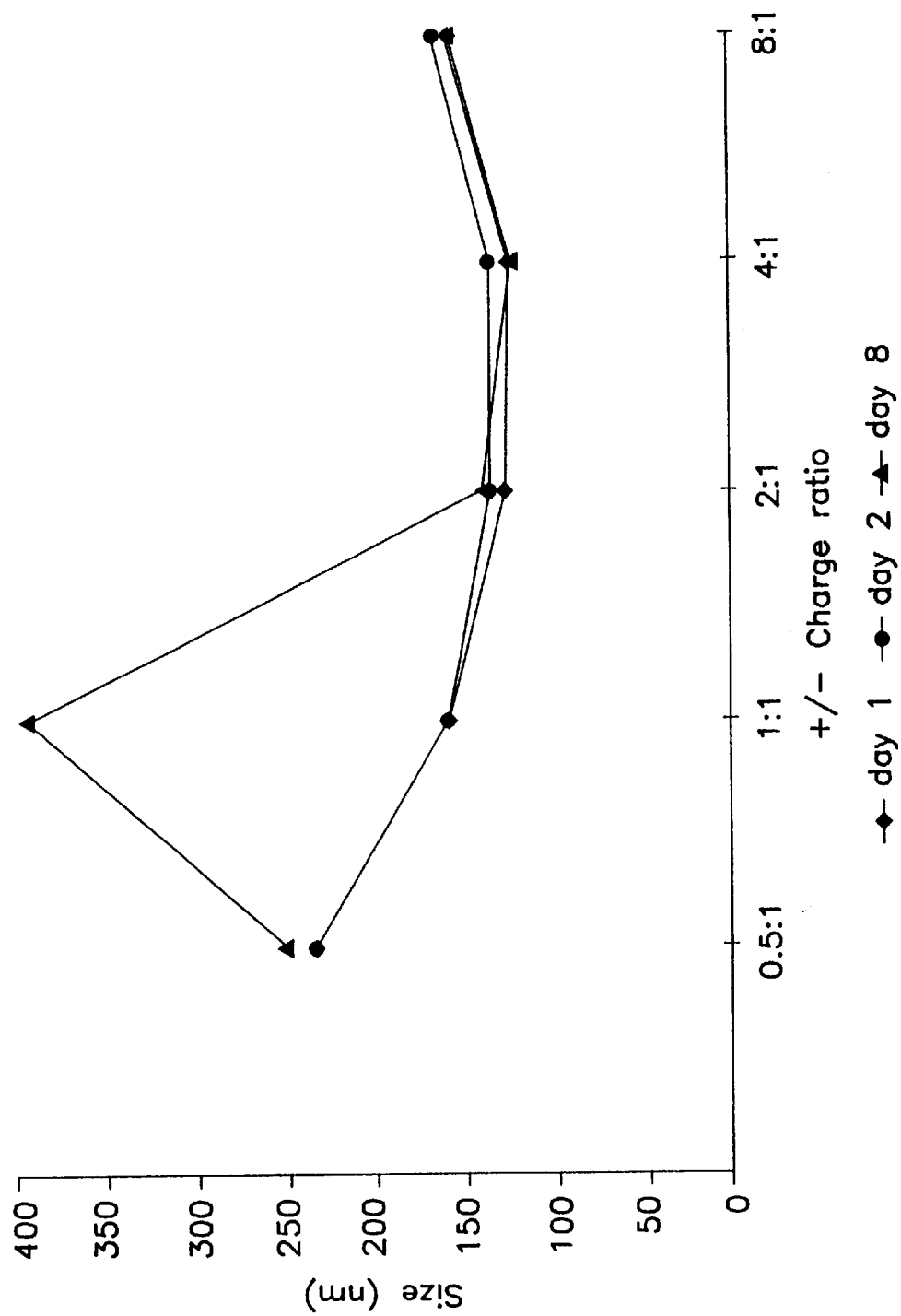

FIG. 10 shows particle size stability over a period of 8 days of a formulation of lipid-conjugated polyamide (Compound 23)/DNA complex, prepared by the "dilution-concentration" formulation method.

Figure 11:
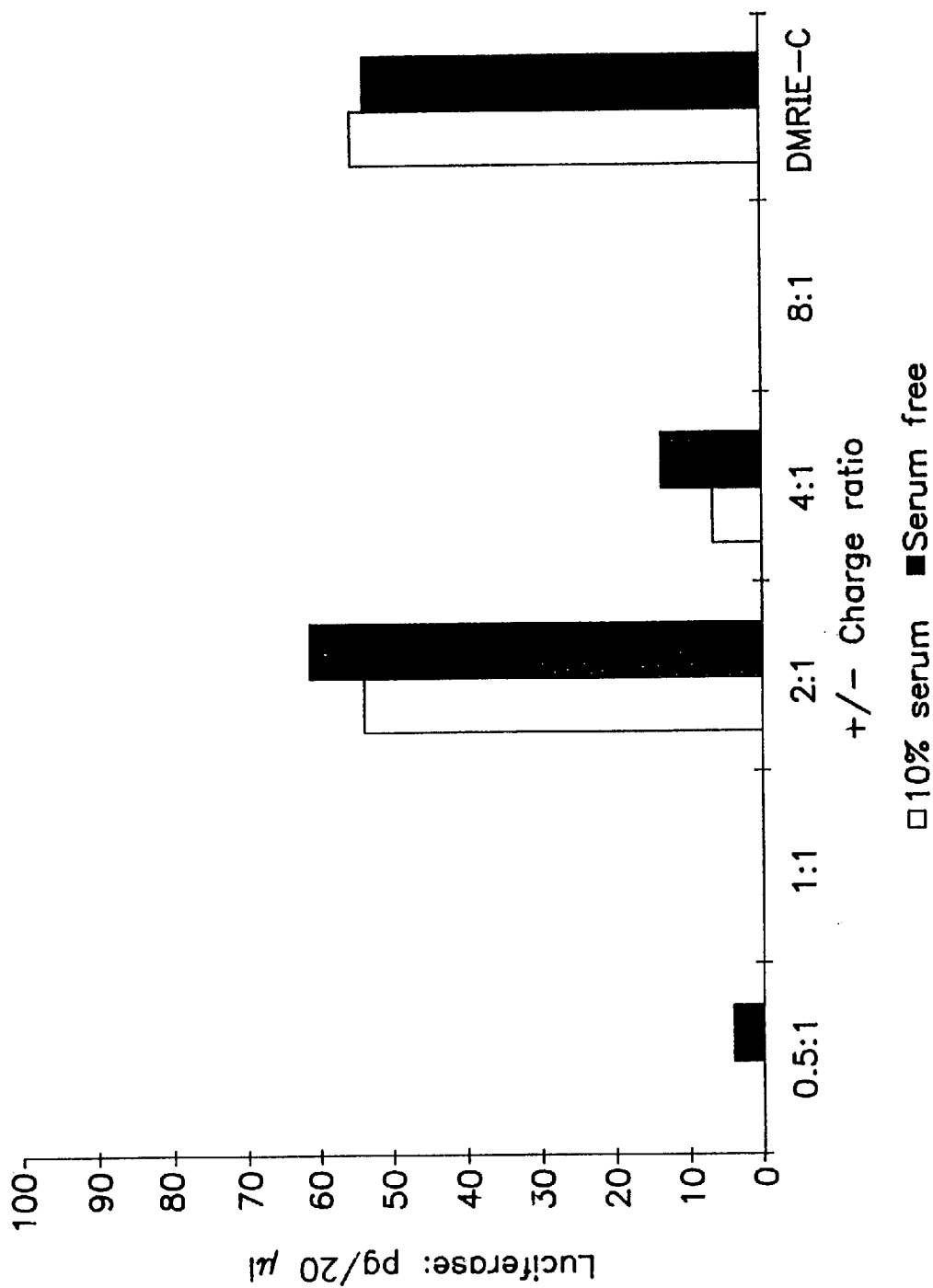

FIG. 11 illustrates the stability of a formulation of lipid-conjugated polyamide (Compound 16)/DNA complex prepared by the "dilution-concentration" formulation method and a formulation of DMRIE-C™/DNA complex prepared by a conventional formulation method. HT1080 cells were transfected with lipid-conjugated polyamide/DNA complex 2 days postformulation and with DMRIE-C™/DNA complex immediately after formulation. Results are shown for transfected cells cultured in both FCS-supplemented and OptiMEM media.

Figure 12:
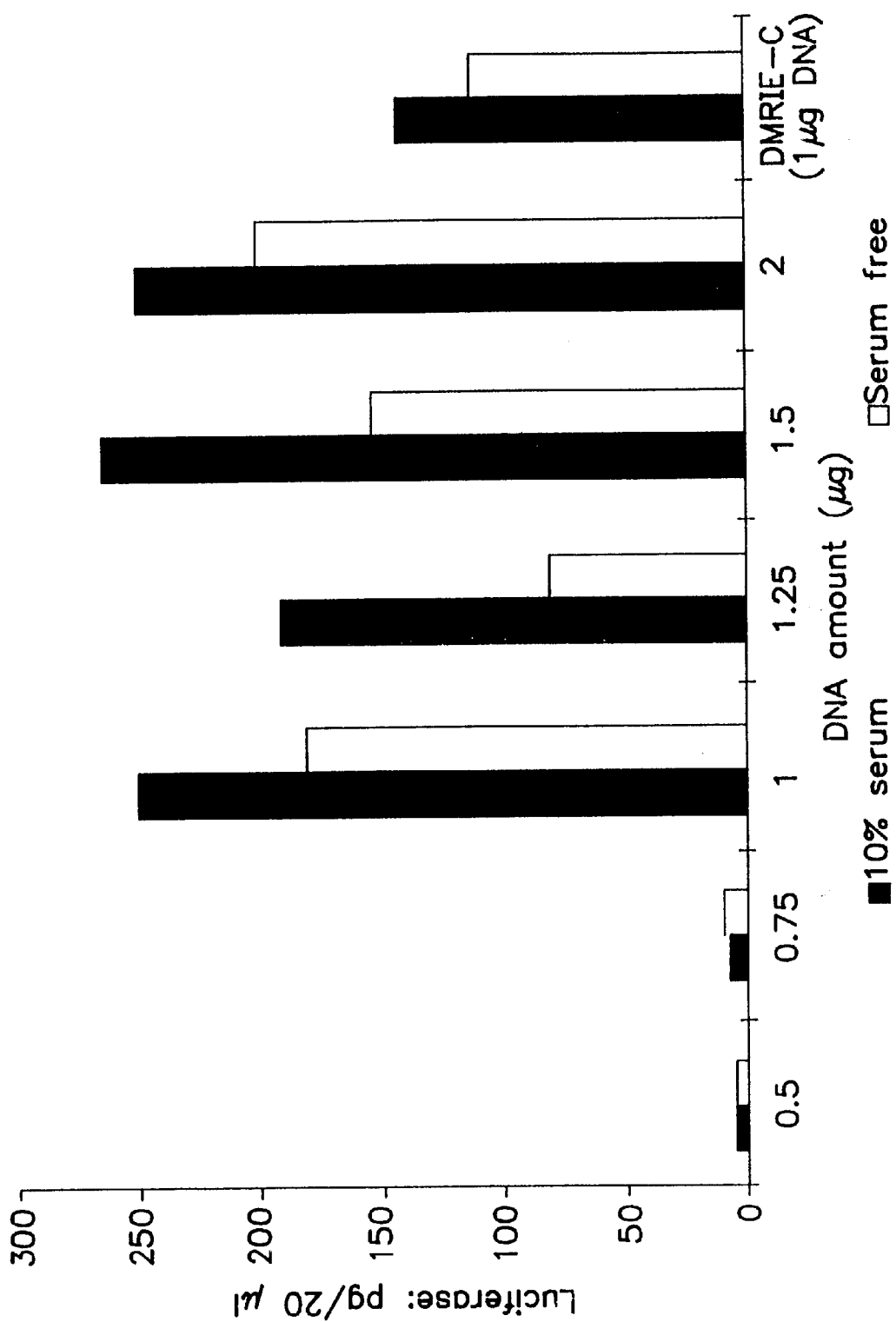

FIG. 12 illustrates the stability of a formulation of lipid-conjugated polyamide (Compound 1 6)/DNA complex prepared by the "dilution-concentration" formulation method and a formulation of DMRIE-C™/DNA complex prepared by a conventional formulation method. HT1080 cells were transfected with lipid-conjugated polyamide/DNA complex 18 days postformulation and with DMRIE-C™/DNA complex immediately after formulation. Results are shown for transfected cells cultured in both FCS-supplemented and OptiMEM media.

Figure 13:
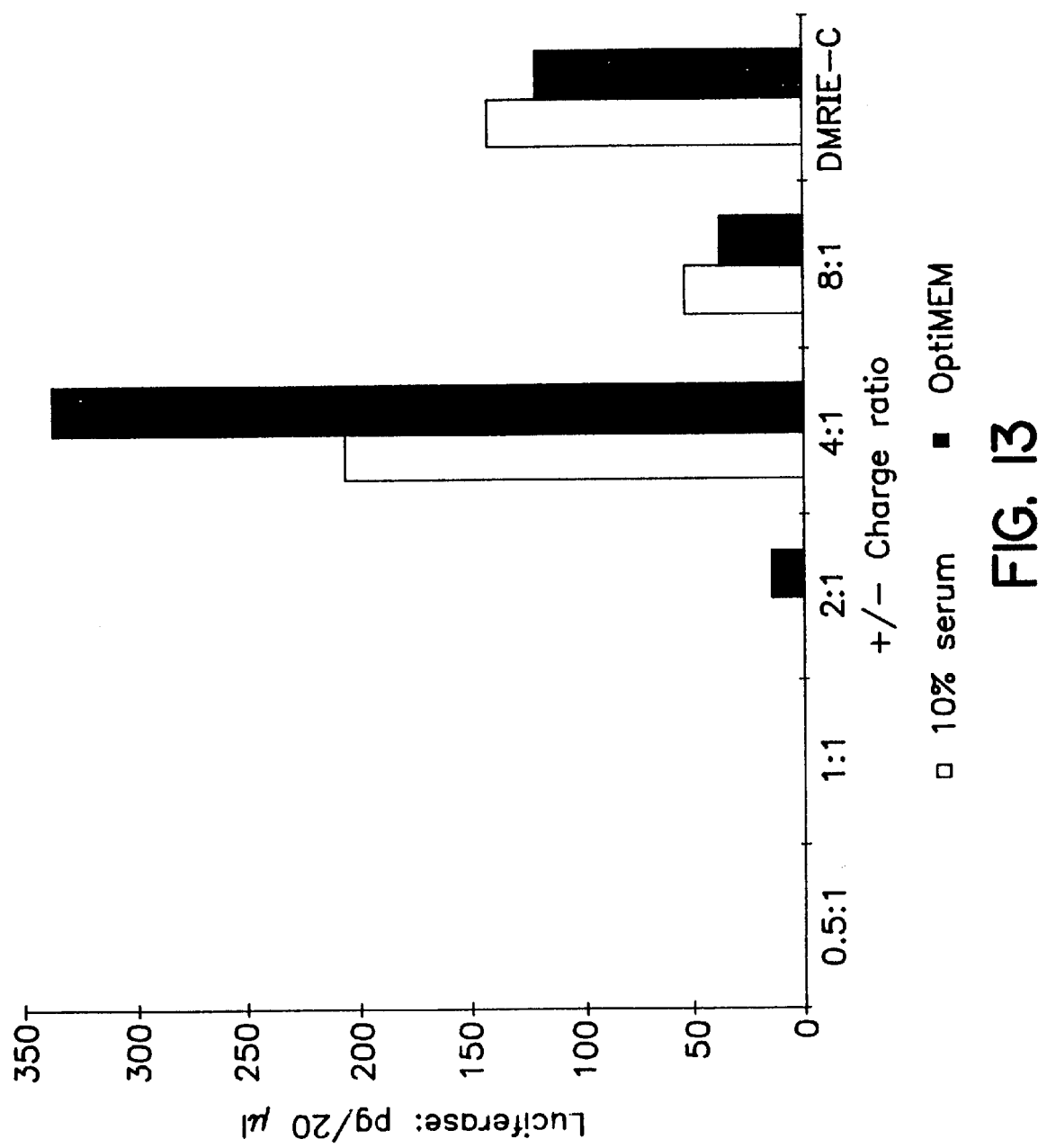

FIG. 13 illustrates the stability of a formulation of lipid-conjugated polyamide (Compound 23)/DNA complex prepared by the "dilution-concentration" formulation method and a formulation of DMRIE-C™/DNA complex prepared by a conventional formulation method. HT1080 cells were transfected with lipid-conjugated polyamide/DNA complex 4 days postformulation and with DMRIE-C™/DNA complex immediately after formulation. Results are shown for transfected cells cultured in both FCS-supplemented and OptiMEM media.

Figure 14:
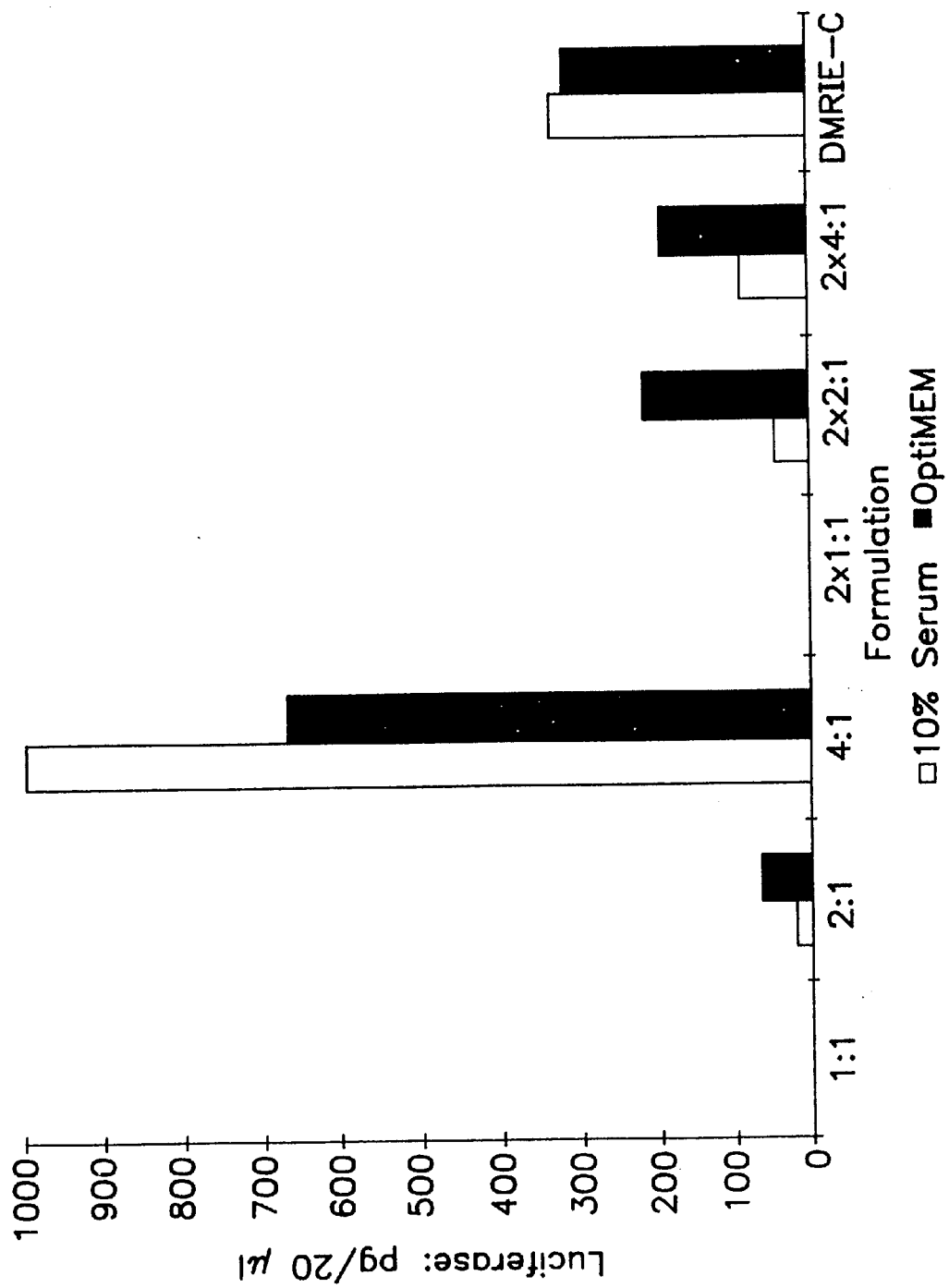

FIG. 14 illustrates the stability of a formulation of lipid-conjugated polyamide (Compound 23)/DNA complex prepared by the "dilution-concentration" formulation method and a formulation of DMRIE-C™/DNA complex prepared by a conventional formulation method. HT1080 cells were transfected with lipid-conjugated polyamide/DNA complex 12 days postformulation and with DMRIE-C™/DNA complex immediately after formulation. Also shown are the effects of doubling the quantity of transfection medium on transfection efficiency. Results are shown for transfected cells cultured in both FCS-supplemented and OptiMEM media.

Figure 15:
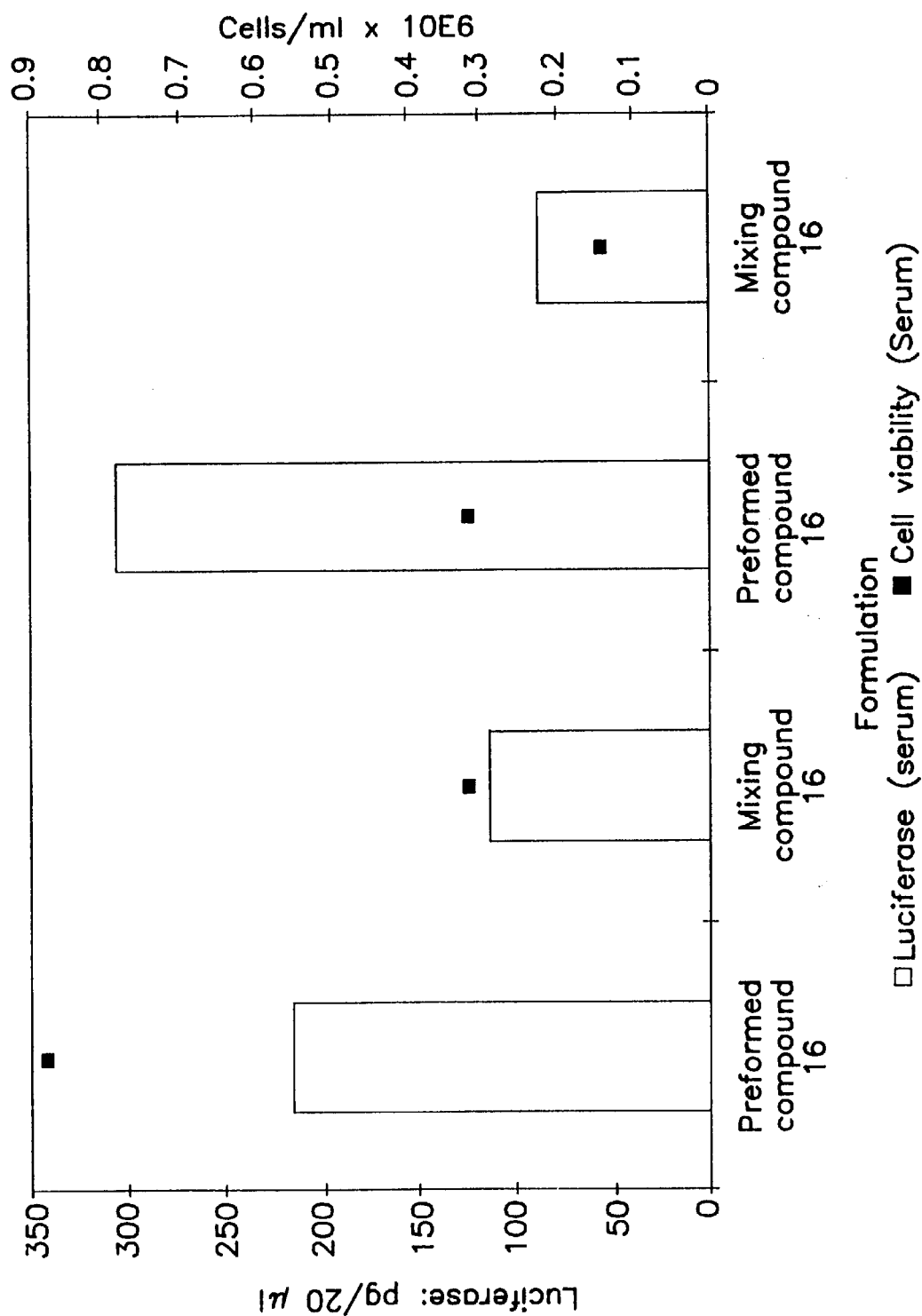

FIG. 15 illustrates transfection efficiency using conventional and "dilution-concentration" formulation methods. "Mixing" refers to a conventional formulation method (in which the delivery vehicle and DNA were mixed immediately prior to transfection). "Preformed" refers to formulation of delivery vehicle/DNA complexes by the "dilution-concentration" formulation method, followed by transfection 1 to 5 days later. Also shown is cell toxicity. Results are shown for transfected cells cultured in FCS-supplemented medium.

GENERAL METHODS AND DETAILED DESCRIPTION

The terms "lipid-conjugated polyamide compound" and "lipid-conjugated compound" are used interchangeably herein to refer to a compounds of the present invention which have both an oligomeric amide moiety and one or more lipid moieties.

The terms "oligomeric" and "oligomeric amide" are used interchangeably herein to refer to two or more monomer units that are linked together by an amide bond,

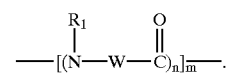

The term "monomer" or "monomeric" unit refers to the unit defined by the formula

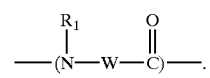

As used herein, the term "lipid" refers to a hydrophobic or amphipathic moiety. A lipid moiety can be conjugated directly to the oligomeric amide moiety, or optionally, indirectly to the oligomeric amide moiety via a linker moiety.

The terms "oligomeric reactant," "oligomer reactant," and "oligomeric amide reactant," and "lipid reactant" refer herein to reactive species from which lipid-conjugated polyamide compounds of the present invention are synthesized.

The term "backbone" refers herein to the scaffold structure of a moiety which is typically either a straight chain, branched or cyclic arrangement of covalently bonded carbon or heteroatoms (i.e., the scaffold structure does not include any of the hydrogen atoms, or alternatively, substitution groups bonded to it).

As used herein, the term "optionally substituted" refers to the replacement of hydrogen with a monovalent radical, such as, for example, hydroxyl-, carboxyl-, phosphor amino-, halo-, alkyl-, aryl-, arylalkyl-, thioamido-, amido-, nitro-, cyano-, haloalkyl-, and the like.

The term "aliphatic" refers herein to straight chain, branched and cyclic compounds that do not have aromatic properties, which contain carbon atoms and optionally, one or more heteroatoms (i.e., one or more functional groups, such as, for example, a substituted amino, an alkoxy, a carbonyl, an ester, and the like), and optionally one or more double or triple bond (i.e., alkenyl or alkynyl, respectively).

As used herein, the term "aryl" refers to aromatic groups, such as, for example, monocyclic and polycyclic aromatic groups, having one or more heteroatoms incorporated therein (e.g., nitrogen, oxygen, sulfur, and phosphorus). The term "polycyclic" refers herein to both fused and non-fused cyclic structure in which at least one cyclic structure is aromatic. Exemplary aryl moieties include, phenyl, naphthyl, and the like.

The term "arylalkyl" refers herein to an alkyl group, having optional functional groups incorporated therein, substituted with an aryl group. Exemplary arylalkyl moieties include benzyl, picolyl, and the like.

As used herein, the term "delivery vehicle" refers to a compound and/or structure that complexes with and facilitates the delivery of a biologically active compound to a target site. Suitable delivery vehicles employed in the practice of the present invention include, for example, lipid-conjugated polyamide compounds of the present invention, lipids, polycationic non-lipid compounds, liposomes, and the like.

As used herein, the term "complex" refers to a structure formed by interaction between two or more compounds or structures. Such interaction can be via chemical interaction, such as, for example, covalent, ionic, or secondary bonding (e.g., hydrogen bonding), and the like, or via physical interaction, such as, for example, encapsulation, entrapment, and the like.

For example, lipid-conjugated polyamide compounds of the present invention can be complexed to a low molecular weight biologically active compound (including for example, oligonucleotides) via covalent bonding through an intermediately positioned sequence of amino acids that is susceptible to degradation by endogenous proteolytic enzymes. Thus, for example, exposure of the complex to degradative enzymes results in cleavage and subsequent release of the biologically active compound from the complex. Lipid-conjugated polyamide compounds of the present invention can also be complexed to biologically active compounds, such as polynucleotides, via ionic or secondary bonding, or alternatively via encapsulation or entrapment.

The terms "polynucleotide" and "polynucleic acid" are used interchangeably herein to refer to DNA, RNA, and analogues thereof, peptide-nucleic acids, as well as DNA or RNA having non-phosphate containing nucleotides. Polynucleotides employed in the practice of the present invention can be single-stranded, double-stranded, or chimeric single- or double-stranded molecules.

All publications mentioned herein are incorporated herein by reference for the purpose of disclosing and describing features of the invention for which the publications are cited in connection with.

LIPID-CONJUGATED POLYAMIDE COMPOUNDS

The present invention provides lipid-conjugated polyamide compounds having the general formula:

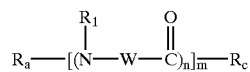

wherein n is an integer selected from 1 to about 48 and m is an integer selected from about 2 to about 48, wherein $R_1$ for each monomeric unit,

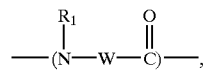

and $R_a$ are independently selected from the group consisting of a hydrogen atom; a hydroxy group; an amino group; a carboxyl group; a sulfonyl group; —SH; an optionally substituted, branched or straight chain aliphatic group having 1 to about 8 carbon atoms in a backbone structure that optionally contains nitrogen, oxygen, sulfur, and phosphorus, wherein said aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl component of said arylalkyl optionally has one or more double or triple bonds; and a lipid moiety that is optionally bonded to linker moiety, wherein $R_1$ is not a hydrogen atom for at least one monomeric unit, wherein $R_c$ is selected from a hydrogen atom; a hydroxy group; an amino group; a hydrazine group; a sulfonyl group; —SH; an optionally substituted, branched or straight chain aliphatic group having 1 to about 8 carbon atoms in a backbone structure that optionally contains nitrogen, oxygen, sulfur, and phosphorus, wherein said aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl group of said arylalkyl optionally has one or more double or triple bonds; and a lipid moiety that is optionally bonded to a linker moiety, wherein when $R_1$, $R_a$, or $R_c$ is an aryl or arylalkyl group having fewer than about 5 carbon atoms in a backbone structure, said backbone structure further comprises one or more heteroatoms, such as, for example, oxygen and/or nitrogen, wherein W for each monomeric unit is independently selected from an optionally substituted, branched or straight chain divalent moiety having from 1 to about 50 atoms and optionally, one or more double or triple bonds in a backbone that contains carbon and optionally contains nitrogen, oxygen, sulfur, and phosphorus, wherein said optional substitution of W may be a lipid moiety that is optionally bonded to a linker moiety, wherein said lipid moiety is a hydrophobic or amphipathic moiety selected from the group consisting of:

(i) optionally substituted aryl or arylalkyl moieties having from about 14 to about 50 carbon atoms in a backbone structure that optionally contains nitrogen, oxygen, sulfur, and phosphorus, wherein the alkyl group of said arylalkyl optionally has one or more double or triple bonds; and (ii) optionally substituted, branched or straight chain aliphatic moieties having from about 10 to about 50 carbon atoms in a backbone structure that optionally contains nitrogen, oxygen, sulfur, and phosphorus, wherein said aliphatic moieties optionally have one or more double or triple bonds, and wherein at least one of $R_a$, $R_c$, W for a single monomeric unit, and $R_1$ for a single monomeric unit comprises a lipid moiety.

Lipid-conjugated polyamides of the present invention can be random polymers where each $R_1$ and W varies from monomer to monomer (e.g., where n is 1 and m is an integer from about 2 to about 48). Alternatively, the lipid-conjugated polyamides can be polymers having m number of n-mers (i.e., where n is greater than 1 and m is an integer from about 2 to about 48) that are either repeating (i.e., each n-mer is the same) or randomly variable (i.e., the monomer composition of each n-mer varies from n-mer to n-mer).

Typically, the integer n is not more than about 40, more typically not more than about 20, and even more typically not more than about 6. Preferably, n is about 3. The integer m is typically not more than about 40, more typically not more than about 25. Usually, the integer m is not more than about 15, typically not more than about 12, and even more typically not more than about 8.

Heteroatoms (i.e., nitrogen, oxygen, sulfur, and phosphorus) incorporated into the backbone structure of aliphatic moieties and the alkyl component of arylalkyl moieties typically form a functional group, such as, for example, a substituted amine, a carbonyl, an alkoxy, an ester, and the like. Thus, aliphatic and arylalkyl moieties employed in compounds of the present invention optionally have one or more functional groups incorporated therein. Heteroatoms incorporated into the backbone structure of aryl moieties are incorporated as ring atoms in cyclic aryl moieties.

When $R_1$, $R_a$, and $R_c$ are aliphatic, they typically contain at least 2 carbon atoms in a backbone structure and more typically contain at least about 3 carbon atoms in a backbone structure. Aryl and arylalkyl $R_1$, $R_a$, and $R_c$ groups can be linear or cyclic. Aryl and arylalkyl $R_1$, $R_a$, and $R_c$ having less than about 5 carbon atoms in a backbone structure, also typically have one or more heteroatoms in the backbone structure, such as, for example, nitrogen and/or oxygen. Typically aryl and arylalkyl $R_1$, $R_a$, and $R_c$ have at least about 5 carbon atoms in a backbone structure.

$R_a$ is typically —OH, —H, —SH, —COOH, sulfonyl, or a lipid moiety optionally conjugated to a linker moiety. $R_a$ is typically —OH, —H, —SH, —NH$_2$, sulfonyl, hydrazine, or a lipid moiety optionally conjugated to a linker moiety. Preferably, either $R_a$ or $R_c$ is a lipid moiety optionally conjugated to a linker moiety.

$R_1$ can be a sidechain that is cationic, anionic, or neutral at physiological relevant pH. Typically, physiological pH is at least about 5.5 and typically at least about 6.0. More typically, physiological pH is at least about 6.5. Usually, physiological pH is less than about 8.5 and typically less than about 8.0. More typically, physiological pH is less than about 7.5.

Suitable cationic sidechains include, for example, aminoalkyl (e.g., aminoethyl, aminopropyl, aminobutyl, aminopentyl, and the like) as well as derivatives thereof; (S)-α-methylethylenediamino and derivatives thereof; trimethylaminoethyl and derivatives thereof; guanidinoalkyl (e.g., guanidinoethyl, guanidinopropyl, guanidinobutyl, guanidinopentyl, and the like) and derivatives thereof; aminobenzyl and derivatives thereof; pyridinium and derivatives thereof; and other like cationic moieties that are known to those of ordinary skill in the art.

Suitable neutral sidechains include, for example, (S) or (R)-α-methylbenzyl and derivatives thereof; benzyl and derivatives thereof; phenethyl and derivatives thereof; naphthylmethyl and derivatives thereof; (S) or (R)-α-methylnaphthyl and derivatives thereof; N-propylpyrrolidinone and derivatives thereof; cyclohexylmethyl and derivatives thereof; furfuryl and derivatives thereof; 3,4,5-trimethoxybenzyl and derivatives thereof; methoxyethyl and derivatives thereof; p-methoxyphenethyl and derivatives thereof; isoamyl ("IsoA") and derivatives thereof; and other like neutral moieties that are known to those of ordinary skill in the art.

Suitable anionic sidechains include, for example, carboxy methyl, carboxy ethyl, and the like, and derivatives thereof, benzoic acid and derivatives thereof; phosphates and derivatives thereof; sulfates and derivatives thereof, and other like anionic moieties that are known to those of ordinary skill in the art.

Optionally, $R_1$ can be a moiety found on naturally- or non-naturally-occuring amino acids, or $R_1$ can be a lipid moiety optionally bonded to a linker moiety. As used herein, the term "naturally-occuring amino acid" refers to Ala, Cys, Asp, Glu, Phe, His, Ile, Lys, Leu, Met, Asn, Gln, Arg, Ser, Thr, Val, Trp, and Tyr. The term "non-naturally-occuring amino acid" refers to amino acids typically not found in nature, including, for example, D-isomers of naturally-occuring amino acids, 2-aminoadipic acid, 2-aminobutyric acid, norvaline, norleucine, ornithine, and the like.

Typically $R_1$ is not hydrogen for at least two monomeric units, more typically $R_1$ is not hydrogen for at least three monomeric units if n x m is 3 or more. Typically, less than about 75% of the monomer units have an $R_1$ that is hydrogen. More typically, less than about 50% of the monomer units have an $R_1$ that is hydrogen. Even more typically, less than about 25% of the monomer units have an $R_1$ that is hydrogen. Even more typically $R_1$ is not hydrogen for any of the monomeric units.

W is typically —CH$_2$CH$_2$—,

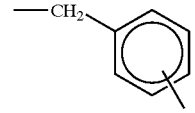

i.e., toluic acid), —CH$_2$CH$_2$—O—, —CH$_2$—CH=CH—, or $$-CR_2R_3-, \qquad (II)$$

where $R_2$ and $R_3$ for each monomeric unit are monovalent moieties independently selected from a hydrogen atom; a hydroxy group; an amino group; a carboxyl group; a sulfonyl group; —SH; an optionally substituted, branched or straight chain aliphatic group having from 1 to about 8 carbon atoms in a backbone structure that optionally contains nitrogen, oxygen, sulfur, phosphorus, and the like, wherein said aliphatic group optionally has one or more double or triple bonds; an optionally substituted aryl group having from about 3 to about 12 carbon atoms in a backbone structure that optionally contains nitrogen, oxygen, sulfur, phosphorus, and the like; an optionally substituted arylalkyl group having from about 3 to about 12 carbon atoms in a backbone structure that optionally contains nitrogen, oxygen, sulfur, phosphorus, and the like, wherein the alkyl component of said arylalkyl optionally has one or more double or triple bonds; and a lipid moiety that is optionally bonded to a linker moiety, wherein when either $R_2$ and $R_3$ is an aryl or arylalkyl group having fewer than about 5 carbon atoms in a backbone structure, the backbone structure typically comprises one or more heteroatoms, such as, for example, oxygen and/or nitrogen.

When $R_2$ and $R_3$ are aliphatic, they typically contain at least 2 carbon atoms in a backbone structure and more typically contain at least about 3 carbon atoms in a backbone structure. Aryl and arylalkyl $R_2$ and $R_3$ groups can be linear or cyclic. Aryl and arylalkyl $R_2$ and $R_3$ having less than about 5 carbon atoms in a backbone structure, also typically have one or more heteroatoms in the backbone structure, such as, for example, nitrogen and/or oxygen. Typically aryl and arylalkyl $R_2$ and $R_3$ have at least about 5 carbon atoms in a backbone structure.

$R_2$ and $R_3$ typically are moieties found on naturally-occuring and non-naturally-occuring amino acids. Usually, at least one of $R_2$ and $R_3$ is a hydrogen atom. Most typically, $R_2$ and $R_3$ are both hydrogen for all monomeric units, such that compound (I) is a lipid-conjugated, N-substituted polyglycine compound.

The lipid moiety can be positioned at $R_a$, $R_c$, $R_1$ for one or more monomers, or at a substitution position in W for one or more monomers. Lipid moieties can be bonded directly to a monomeric unit, or they can be bonded indirectly to a monomeric unit via a linker moiety.

The term "linker" used herein refers to a moiety that functions to couple the oligomeric amide and lipid moieties together in a manner such that the molecular distance between the two moieties is greater than would be if the lipid and oligomeric amide moieties were coupled directly to each other. Linker moieties can be relatively small, having from 1 to about 20 atoms in a backbone, or alternatively polymeric. Small linker moieties are optionally substituted and typically have from 1 to about 20 atoms in a backbone (e.g., carbon, nitrogen, oxygen, sulfur, phosphorus, and the like). Typically, small linker moieties have less than about 18 atoms in a backbone, and more typically, less than about 15 atoms in a backbone. Usually, small linker moieties have less than about 10 atoms in a backbone, and optionally have less than about 5 atoms in a backbone.

Linker moieties can be derived from bifunctional molecules such as, for example, 6-aminohexanoic acid, 2-(2-(2-aminoethoxy)ethoxy)ethoxy) acetic acid, and the like) that are capable of reacting with both oligomeric and lipid reactants. Linker moieties also can be derived from groups such as, for example, acyl and substituted-acyl groups, sulfonyl and substituted-sulfonyl groups, and other like reactive moieties that are employed during chemical synthesis to facilitate conjugation of the lipid moiety to the oligomeric moiety.

Polymeric linker moieties are optionally substituted (e.g., hydroxy-, carboxy-, phosphor amino-, and the like), substantially linear polymers having a backbone that contains carbon, and optionally contains nitrogen, oxygen, sulfur, phosphorus, and the like. Polymeric linker moieties have an average molecular weight between about 300 daltons and about 15,000 daltons, typically less than about 10,000 daltons, more typically less than about 5,000 daltons, and even more typically less than about 3000 daltons, and optionally less than about 1000 daltons. Suitable polymeric linker moieties include, for example, polyethylene glycols, polypropylene glycols, polyvinyl alcohols, polyvinylpyrrolidones, and the like.

Lipid moieties are hydrophobic moieties or amphipathic moieties that are either neutral (i.e., having no charge or a net charge of zero) or charged, and either naturally or synthetically derived. Typically, the lipid moiety in lipid-conjugated polyamide compounds of the present invention is amphipathic.

Suitable lipid moities include: (1) optionally substituted, aryl or arylalkyl moities having from about 14 to about 50 carbon atoms in a backbone structure that optionally contains nitrogen, oxygen, sulfur, phosphorus, and the like, where the alkyl component of the arylalkyl moiety optionally has one or more double or triple bonds; (2) optionally substituted, branched or straight chain aliphatic moieties having from about 10 to about 50 carbon atoms in a backbone structure that optionally contains nitrogen, oxygen, sulfur, phosphorus, and the like, and optionally has one or more double or triple bonds.

Typically, aryl and arylalkyl lipid moieties have at least about 16 carbon atoms and more typically have at least about 20 carbon atoms, and even more typically at least about 30 carbon atoms.

Aliphatic lipid moities employed in compounds of the present invention typically have at least about 12 carbon atoms and more typically have at least about 14 carbon atoms. Usually, the aliphatic lipid moieties have at least about 18 carbon atoms, more usually at least about 24 carbon atoms, and even more usually at least about 30 carbon atoms.

The number of lipid moieties in lipid-conjugated polyamide compounds of the present invention can vary depending on the degree of hydrophobicity desired, and will also vary with oligomer length (i.e., n×m) and size of lipid moiety. For example, when the lipid moiety has about 30 carbon atoms or less, lipid-conjugated polyamide compounds of the present invention typically have conjugated to it, a number of lipid moities that is less than the number computed as 90% of the total number of monomeric groups (i.e., n×m) (i.e., if n is 3 and m is 3, then the number of lipid moieties conjugated to the lipid-conjugated polyamide compound is typically less than about 8). More typically, when the lipid moiety has about 30 carbon atoms or less, lipid-conjugated polyamide compounds of the present invention have conjugated to it, a number of lipid moieties that is less than about 80% of the total number of monomeric groups, more typically less than about 75% of the total number of monomeric groups, and even more typically less than about 60% of the total number of monomeric groups.

When the lipid moiety has more than about 30 carbon atoms, typically, lipid-conjugated polyamide compounds of the present invention have conjugated to it a number of lipid moities that is less than the number computed as 50% of the total number of monomeric groups.

Suitable lipid moieties include those having one or more hydrophobic tails that are optionally substituted aliphatic, straight chain moieties, each hydrophobic tail independently having from about 8 to about 30 carbon atoms in a backbone that in addition, optionally contains nitrogen, oxygen, sulfur, phosphorus, and the like. Typically, hydrophobic tails have at least about 10 carbon atoms in a backbone and more typically have at least about 12 carbon atoms in a backbone. Hydrophobic tails employed in lipid-conjugated polyamide compounds of the present invention typically do not have more than about 26 carbon atoms in a backbone, and more typically do not have more than about 24 carbon atoms in a backbone.

Natural lipid moieties employed in the practice of the present invention can be derived from, for example, phospholipids, including, for example, phosphoglycerides (including both acyl phosphoglycerides (such as, for example, phosphatidic acid, phosphatidyl ethanolamine, phosphatidyl serine, phosphatidyl inositol, phosphatidyl inositol phosphate, phosphatidyl inositol bisphosphate, phosphatidyl glycerol, diphosphatidylglycerol, and the like) and ether phosphoglycerides); glycosylglycerides (such as, for example, monogalactosyl diacylglycerol, digalactosyldiacylglycerol, sulphoquinovosyldiacylglycerol, dimannosyldiacylglycerol, galactofuranosyldiacylglycerol, galactosylglucosyldiacylglycerol, galactosylglucosyldiacylglycerol, glucosylgalactosylglucosyldiacylglycerol, and the like); sphingolipids (such as, for example, sphingosines, glycosyl ceramides, gangliosides, and the like); and saturated and unsaturated sterols (such as, for example, cholesterol, ergosterol, stigmasterol, sitosterol, and the like); and other like natural lipids.

Suitable synthetic lipid moieties can be derived from, for example, dipalmitoyl phosphotidylethanolamine (DMPE) (Genzyme Corp., Cambridge), DMRIE-C™ (GibcoBRL, Gaithersburg, Md.), 2,3-dioleyloxy-N-[2(spermine-carboxamido)ethyl]-N,N-dimethyl-1 - propanaminiumtrifluoroacetate (DOSPA) (Lipofectamine™, GibcoBRL, Gaithersburg, Md.), 3p-[N-(N',N'-dimetylaminoethyl) carbamoyl]cholesterol, Tfx-50 (Promega Corp., Madison, Wis.), N,N 1, N2,N3 - tetramethyl-N,N 1, N2, N3 -tetrapalmitylsperimine (TM-TPS) (Cellfectin, GibcoBRL, Gaithersburg, Md.), dipalmitoyl phosphatidylethanolaminospermine, and the like.

Suitable lipid moieties also include those derived from fatty acids and fatty alcohols having from about 8 to about 24 carbon atoms in a backbone. Typically, the fatty acids and fatty alcohols have at least about 10 carbon atoms in a backbone, and more typically have at least about 12 carbon atoms in a backbone. Usually, the fatty acids and alcohols from which lipid moieties are derived have less than about 20 carbon atoms in a backbone.

Typically, $R_a$ is a lipid moiety or a lipid moiety conjugated to a linker moiety. A particularly useful lipid moiety-containing $R_a$ radical is the phosphatidyl alkylamino-substituted acyl radical having the formula, (III)

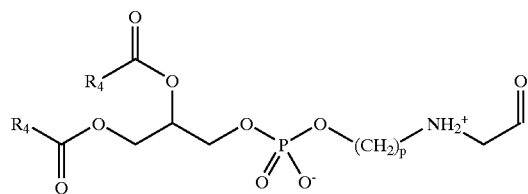

where p is an integer selected from 2 or 3, and each $R_4$ is independently selected from an alkyl or alkenyl moiety having from about 6 and to about 25 carbon atoms in a backbone. Typically $R_4$ has up to about 22 carbon atoms in a backbone, more typically, up to about 20 carbon atoms, even more typically up to about 18 atoms. Typically, $R_4$ has at least about 8 carbon atoms in a backbone, more typically at least about 10 carbon atoms, and even more typically at least about 12 carbon atoms in a backbone. Exemplary $R_4$ moieties include dodecyl, tridecyl, tetradecyl, pentadecyl, hexadecyl, heptadecyl, octadecyl, and the like. Preferably p is 2.

Lipid-conjugated polyamide compounds of the present invention can be optionally further conjugated or complexed with agents that impart, for example, targeting capabilities, structural features, biological activity, or that introduce degradations sites, and the like. Suitable agents include, for example, mono-, di-, and polysaccaharides, polyethylene glycols, amino acids, peptides, polypeptides, proteins (including, for example, lipoproteins, glycoproteins, antibodies, and the like), crosslinking agents, marker agents (such as, for example, fluoroscein, biotin, $^{32}P$, and the like), and the like.

Those of ordinary skill in the art will appreciate that $R_1$, $R_c$, $R_a$, W, and the particular lipid moiety employed can be readily varied to optimize the physicochemical properties of the lipid-conjugated polyamide compound for delivery of a particular type of biologically active compound. For example, oligomeric moieties of the present invention suitable for use in the delivery of polynucleic acids to cells have a net positive charge and are capable of condensing polynucleic acids so that they are more compact in size, thus facilitating their delivery to cells.

Compounds of formula (I) that are suitable for use in the delivery of polynucleic acids to cells, include lipid-conjugated polyamide compounds having repeating n-mer units (i.e., where n is greater than 1). For example, when n is 3, the lipid-conjugated polyamide compound of formula (I) has repeating trimer units, i.e., (IV)

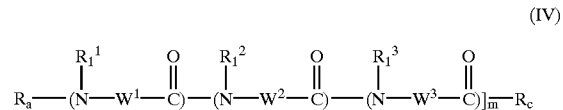

where $R_a$, $R_c$, m, each W and each $R_1$ are defined as in formula (I). Compounds having formula (IV) that are suitable for use in the delivery of polynucleic acids to cells include, for example, those where $R_1^1$ is a cationic side chain, $R_1^2$ and $R_1^3$ are both neutral side chains, each W is $CH_2$, $R_c$ is $NH_2$, and $R_a$ is defined by formula (III), such as those compounds shown in Table 2, in Example 1, herein.

Lipid-conjugated polyamide compounds of the present invention typically form concentration-dependent, ordered two- or three-dimensional structures in solution. Such structures include two dimensional arrays, such as, for example, a single charged layer or a lipid bilayer surface, and three-dimensional structures, such as, for example, micelles, vesicles, and liposomes. Typically, ordered structures formed from lipid-conjugated polyamide compounds of the present invention by themselves, typically are sufficiently small such that they do not scatter light. Micelles, vesicles, and hiposomes prepared from lipid-conjugated compounds complexed with polynucleotides typically have average particle sizes that are less than about 1 μm, more typically less than about 500 nm, and even more typically less than about 200 nm.

In addition to the delivery of biologically active agents to cells, lipid-conjugated polyamide compounds of the present invention can also be used in applications, such as, for example, screening peptide-like compounds for biological activity, incorporation into biosensors such that the oligomeric moiety has the capacity to bind to a target ligand, and the like. For drug screening applications, for example, libraries of lipid-conjugated polyamide compounds having a variety of $R_1$ groups can be synthesized and subsequently screened for biological activity in accordance with the methods for synthesizing and screening modified peptide libraries described in PCT publication WO 91/19735 (published Dec. 26, 1991), incorporated herein by reference.

Synthesis of Lipid-Conjugated Polyamide Compounds

Lipid-conjugated polyamide compounds of the present invention can be synthesized by both solid-phase and solution-phase methods. The present invention also provides a method of synthesizing lipid-conjugated polyamide compounds, said method comprising:

a) contacting
  (1) a lipid reactant, with
  (2) an oligomer reactant, wherein said oligomer reactant has the general formula:

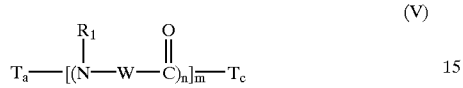

(V)

wherein n is an integer selected from 1 to about 48, and m is an integer from about 2 to about 48, wherein each $T_a$ and $T_c$ is independently selected from a terminal group and a reactive moiety that is capable of further reaction with said lipid reactant, wherein $R_1$ for each monomeric unit,

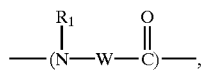

in said oligomer reactant is selected from the group consisting of a hydrogen atom; a hydroxy group; an amino group; a carboxyl group; a sulfonyl group, —SH; an optionally substituted, branched or straight chain aliphatic group having from 1 to about 8 carbon atoms in a backbone structure that optionally contains nitrogen, oxygen, sulfur, and phosphorus, wherein the aliphatic group optionally has one or more double or triple bonds; an optionally substituted aryl group having from about 3 to about 12 carbon atoms in a backbone structure that optionally contains nitrogen, oxygen, sulfur, and phosphorus; an optionally substituted arylalkyl group having from about 3 to about 12 carbon atoms in a backbone structure that optionally contains nitrogen, oxygen, sulfur, and phosphorus, wherein the alkyl component of said arylalkyl optionally has one or more double or triple bonds; and a reactive moiety that is capable of further reaction with said lipid reactant, wherein when $R_1$, $R_a$, or $R_c$ is an aryl or arylalkyl group having fewer than about 5 carbon atoms in a backbone structure, the backbone structure typically comprises one or more heteroatoms, such as, for example, oxygen and/or nitrogen, wherein $R_1$ is not a hydrogen atom for at least one monomeric unit, wherein W for each monomeric unit is selected from an optionally substituted, branched or straight chain divalent moiety having from 1 to about 50 atoms in a backbone that contains carbon, and optionally contains nitrogen, oxygen, sulfur, and phosphorus, and optionally one or more double or triple bonds, wherein said optional substitution of W may be a reactive moiety that is capable of further reaction with said lipid reactant, wherein at least one of $T_a$, $T_c$, W for a single monomeric unit, or $R_1$ for a single monomeric unit comprises a reactive moiety that is capable of further reaction with said lipid reactant; then b) reacting said lipid reactant with said oligomer reactant to conjugate the lipid reactant to the oligomer reactant.

The term "lipid reactant" used herein refers to a reactive species having a lipid moiety that is capable of participating in a chemical reaction, such as, for example, nucleophilic displacement, condensation, and the like. Lipid reactants having functional groups, such as, for example, —NH₂, —COOH, —SH, —OH, —SO₂Cl, and —CHO are particularly useful for synthesizing lipid-conjugated compounds of the present invention. Lipid reactants suitable for use in the practice of the present invention include lipid reactants having any one of the lipid moieties described herein which can react with, or which can be modified to react with, the oligomeric reactant or a linker. Typically, lipid reactants are primary, secondary, or tertiary amines. Preferred lipid reactants are phosphatidylethanolamines.

As used herein, the term "oligomer reactant" refers to an oligomeric amide that is capable of participating in a chemical reaction, such as, for example, nucleophilic displacement, condensation, and the like. Oligomer reactants typically are acylated with a leaving group that is susceptible to nucleophilic displacement by a nucleophile, such as an amine. Oligomer reactants suitable for use in the practice of the present invention include all of the oligomeric amide substituents described for formula (I) (i.e.,

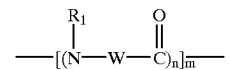

herein.

As used herein, the term "reactive moiety" refers to a moiety that is capable of participating in a reaction with the lipid reactant. Typical reactive moieties include, for example, —NH₂, —OH, —H, —SH, —COOH, acyl (e.g., acetyl), benzoyl, sulfonyl (e.g., dansyl), amide, hydrazine (typically a $T_c$ group), and derivatives thereof (including alkyl-substituted derivatives), and the like. Typically, the reactive moiety is an acyl moiety substituted with a leaving group that is susceptible to nucleophilic displacement by a nucleophile, such as an amine.

Exemplary terminal groups include $R_a$ and $R_c$ moieties that are not reactive moieties, moieties that are biologically active agents, targeting agents (e.g., a cell receptor ligand, antibody, etc.), marker agents, amino acid residues that function, for example, as a degradation site for endogenous proteolytic enzymes, and the like. These terminal groups typically are not further reactive with the lipid reactant.

The oligomer reactant and lipid reactant can be optionally bonded to each other via a linker moiety (which optionally can be derived from a reactive moiety). Alternatively, the linker moiety, which is derived from a molecule that is capable of reacting with both oligomeric and lipid reactants, can be optionally conjugated to either the lipid or oligomer reactant prior to reaction between lipid and oligomer reactants. Thus, the lipid reactant can be conjugated to the oligomer reactant either directly, or indirectly via the linker moiety.

The term "reacting" used herein refers to one or more chemical reactions that result in formation of a chemical bond between the lipid reactant and the oligomer reactant, either directly, or indirectly via the linker moiety. Suitable reactions include, for example, condensation (e.g., acylation, and the like) and nucleophilic displacement.

Oligomer reactants having the general formula (IV) can be prepared, for example, via a series of nucleophilic displacement reactions according to the solid-phase method described by Zuckermann et al., PCT W094/06451 (published Mar. 31, 1994), incorporated herein by reference. The method can be performed utilizing automated peptide synthesis instrumentation to permit rapid synthesis of oligomer reactants of interest. These instruments are commercially available from, for example, Applied Biosystems.

Specifically, monomer assembly into oligomer reactants is achieved by the sequential addition of "submonomer" units to the growing chain. In one method of monomer assembly, each cycle of monomer addition consists of two steps:

(1) acylation of a secondary amine bound to the solid support with an acylating agent that has a leaving group (i.e., a group susceptible to nucleophilic displacement by a nucleophile, such as an amine) and a carbonyl group (e.g., a carboxyl group) (i.e., the "acylation step"); followed by (2) nucleophilic displacement of the leaving group with a sufficient amount of a submonomer that has a primary, secondary, or tertiary amino group to introduce a side-chain (i.e., the "nucleophilic displacement step").

A schematic of the reaction scheme is shown in FIG. 1. Exemplary acylating agents include haloacetic acid, halomethyl benzoic acid, and the like. The efficiency of displacement of the leaving group is modulated by the type of acylating agent employed. For example, when a haloacetic acid is employed, it has been observed that iodine is more efficient at displacing the leaving group compared to chlorine. Suitable submonomers include alkylamines, alkenylamines, aromatic amines, alkoxyamines, semicarbazides, acyl hydrazides, and derivatives thereof, and the like.

Oligomer synthesis using the submonomer approach occurs in the carboxy to amino direction. The oligomer is elaborated until the desired length, then is terminated, for example, with a bromoacetamide group. One advantage of using solid phase submonomer assembly to construct oligomer reactants of the present invention is that the need for N-α-protected monomers is eliminated, as only reactive side-chain functionalities need to be protected.

Typically, the oligomeric reactant is synthesized as a series of repeating di-, tri-, or tetra-mer units. An exemplary trimer-based cationic oligomer has the following monomer sequence in the amino terminal ($T_a$) to carboxy terminus ($T_c$) direction:

(1) positively charge monomer
(2) neutral monomer, and
(3) neutral monomer.

The terms "neutral monomer" and "positively charged monomer" as used herein refer to the net charge of the monomeric unit.

Further reaction of the oligomer reactant with the lipid reactant can occur by further acylation and/or nucleophilic displacement. For example, an oligomer reactant that is haloacylated (e.g., where $T_a$ is a bromoacetyl group) can be reacted with an lipid reactant that is a primary, secondary, or tertiary amine. Conjugation thus occurs by nucleophilic displacement of the bromine, to form a lipid-conjugated polyamide compound.

Lipid-Conjugated Polyamide Compositions and Uses Thereof

In yet another embodiment, the present invention provides compositions comprising lipid-conjugated polyamide compound(s) of the present invention and an effective amount of a biologically active agent. As used herein, the terms "effective amount" and "effective dose" refer to an amount of biologically active agent or biologically active agent-containing lipid-conjugated polyamide composition of the present invention that is sufficient to detectably induce, or participate in, a biological response, such as, for example, signal transduction, transcription, translation, lymphocyte activation, including, for example, antibody production, and the like, in for example, a cell, a mammal, or a bird. The term "biologically active agent" used herein refers to an agent that upon administration in an effective amount to, for example, a cell, a mammal, or a bird, induces or participates in, a biological response.

When the biologically active agent is a polynucleotide, the relative quantities of lipid-conjugated polyamide compound to polynucleic acid are typically selected such that the +/− charge ratio of lipid-conjugated polyamide compound to polynucleotide in the composition is at least about 2 and less than about 10. More typically, the +/− charge ratio is less than about 8, and even more typically is less than about 4. The charge ratio is computed according to the following:

$$\text{Charge Ratio} = (n_L \times M_L)/(3.03 \times M_{DNA}),$$

where $n_L$ is the number of moles of lipid-conjugated polyamide compound, $M_L$=net number of charges/mole lipid-conjugated polyamide, and where MDNA=micrograms of DNA.

Compositions of the present invention can be in liquid or solid form, and can optionally include pharmaceutically acceptable excipients. Such excipients can be used as fillers, processing aids, delivery enhancers and modifiers, and the like. Suitable excipients include, for example, calcium phosphate, magnesium stearate, talc, monosaccharides, dissaccharides, polysaccharides, gelatin, cellulose, methyl cellulose, sodium carboxymethyl cellulose, dextrose, polyvinyl alcohol, polyvinylpyrrolidinone, low melting waxes, ion exchange resins, and the like, as well as combinations of any two or more thereof. A thorough discussion of pharmaceutically acceptable excipients is available in "Remington's Pharmaceutical Sciences" (Mack Pub. Co., N.J. 1991), which is incorporated herein by reference.

Additional agents can be included in the compositions, such as, for example, marker agents, nutrients, and the like. For example, when the biologically active agent is a polynucleotide, agents that promote endocytosis of the desired nucleic acids or aid in binding of the nucleic acids to the cell surface, or both, can be incorporated into compositions of the present invention.

Liquid compositions of the present invention can be in the form of a solution, suspension, or emulsion with a liquid carrier. Suitable liquid carriers include, for example, water, saline, pharmaceutically acceptable organic solvent(s), pharmaceutically acceptable oils or fats, mixtures thereof, and the like. The liquid carrier may contain other suitable pharmaceutically acceptable additives, such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like.

In yet another embodiment, the present invention provides a method for inducing the uptake of a biologically active agent by a cell, said method comprising:

providing a composition comprising an effective amount of a biologically active agent and a lipid-conjugated polyamide compound; then contacting a biological sample with an effective dose of said composition, wherein said biological sample comprises a cell.

As used herein, the term "biological sample" refers to a sample comprising one or more cells or tissue. Cells suitable for use in the practice of the present invention include, for example, mammalian cell lines available from the American Type Culture Collection (ATCC), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, other mammalian (including human) cells (e.g., stem cells, particularly hemapoitic cells, lymphocytes, macrophages, dendritic cells, tumor cells and the like), and the like.

Suitable tissue for use as samples in the present invention include, for example, tissue derived from mammals, such as, muscle, skin, brain, lung, liver, spleen, blood, bone marrow, thymus, heart, lymph, bone, cartilage, pancreas, kidney, gall bladder, stomach, intestine, testis, ovary, uterus, rectum, nervous system, eye, gland, connective, and the like.

Modes of administration to a sample include, for example, ex vivo administration to samples derived from a subject and in vitro administration to a sample. Methods for carrying out these modes of administration are well known to those of ordinary skill in the art. For example, when the biological agent is a polynucleotide, ex vivo delivery and reimplantation of transformed cells into a subject can be achieved as described in e.g., International Publication No. WO 93/14778 (published Aug. 5, 1993), which is incorporated herein by reference.

In yet another embodiment, the present invention provides a method for inducing the uptake of a biologically active agent by a cell in vivo, said method comprising:

providing a composition comprising an effective amount of a biologically active agent and a lipid-conjugated polyamide compound; then administering an effective dose of said composition to a subject.

The present invention further provides a method of expressing a gene in a mammal, said method comprising:

administering a polynucleic acid complexed with a lipid-conjugated polyamide of the present invention to a mammal, wherein said polynucleic acid is capable of functionally expressing said gene in said mammal, and wherein said complex is effective at transfecting said gene into a cell in said mammal.

As used herein, the term "subject" refers to birds and mammals, including for example, rodents and humans. Direct administration to a subject can typically be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, and the like, as well as administration via needles, and gene guns or hyposprays.

Lipid-conjugated compounds of the present invention, when combined with a biologically active agent, are effective at inducing the uptake the biologically active agent by cells. As used herein, the term "induce" and its various grammatical equivalents, refers to effecting the uptake of a biologically active agent by a cell. Methods used for detecting the uptake of biologically active agents by cells will vary depending on the type of biologically active agent employed, however, those of ordinary skill in the art will appreciate that cell uptake can be detected by a variety of known assays and histological techniques, as well as by a variety of diagnostic methods, including, for example, clinical diagnostic methods (e.g., alleviation of symptoms, etc.).

Typically, compounds of the present invention are effective at enhancing the uptake the biologically active agent by cells. When uptake of a biologically active agent by a cell is enhanced, typically the uptake of biologically active agent by the cell is at least about 5% greater than the uptake of the biological agent in neat form (e.g., substantially free of lipid-conjugated polyamide compound). More typically, when uptake is enhanced, the uptake of the biologically active agent by the cell is at least about 10% greater than the uptake of the biologically active agent in neat form, even more typically at least about 15% greater, and even more typically at least about 20% greater.

An effective amount of biologically active agent and likewise, an effective dose of lipid-conjugated polyamide/biological agent containing composition will, of course, vary depending upon known factors such as the pharmacodynamic characteristics of the particular biologically active agent, its mode and route of administration; the age, health, and weight of the recipient; nature and extent of symptoms; kind(s) of concurrent treatment, frequency of treatment, the effect desired, and the like. However, the precise amount for a particular patient and biologically active agent can be readily determined by routine experimentation by a clinician of ordinary skill in the art. Those having ordinary skill in the art will also appreciate that the precise amount of lipid-conjugated compound employed in compositions of the present invention can be readily determined by routine screening studies to determine the optimal ratio of lipid-conjugated polyamide compound to biologically active agent for inducing the desired response. Compositions of lipid-conjugated polyamide compounds complexed with biologically active agents can be administered as a single dose or in multiple doses. Multiple doses can be administered either continuously, in intervals, or a combination of both. For purposes of the present invention, an effective in vivo amount will be from about 0.01 mg/kg/day to about 50 mg/kg/day or about 0.05 mg/kg/day to about 10 mg/kg/day of biologically active agent.

Compositions of the present invention are particularly effective at inducing the uptake of polynucleotides into cells. Polynucleotide uptake by cells can be detected by using protein expression assays or polynucleotide hybridization techniques. Compositions can be screened and optimized with respect to transfection efficiency by incorporating a reporter gene into the DNA and assaying for the reporter gene product using standard immunoassay methods or biological or enzymatic activity assays (such as, for example, a luciferase assay).

When combined with polynucleotides, lipid-conjugated polyamide compounds are particularly effective at inhibiting nuclease-induced polynucleotide degradation caused by nucleases present in serum, and other biological fluids. As a result, smaller quantities of polynucleotides can be more efficiently administered using compositions of the present invention.

Thus, the present invention also provides a method for substantially inhibiting nuclease-induced polynucleotide degradation, said method comprising contacting a polynucleotide with a degradation-inhibiting quantity of lipid-conjugated polyamide compound, and introducing the polynucleotide and the lipid-conjugated polyamide compound into a nuclease-containing environment. Inhibition of nuclease-induced polynucleotide degradation can be detected by incubating a sample of lipid-conjugated polyamide protected polynucleotide and a control sample of unprotected polynucleotide in, for example, serum, for various time periods, then analyzing the mixtures by gel electrophoresis to determine when degradation occurs (for example, when about 50% of the polynucleotide has degraded) for the protected polynucleotide, as compared to unprotected polynucleotide. The degree of degradation can be monitored using known quantitation methods, such as, for example, radiolabelling and the like.

Typically, a degradation-inhibiting quantity of lipid-conjugated polyamide compound is the amount of lipid-conjugated polyamide compound sufficient to substantially inhibit nuclease-induced polynucleotide degradation of a polynucleotide for at least about 5 minutes, as compared to unprotected (i.e., neat) polynucleotide. More typically, the quantity of lipid-conjugated polyamide compound is sufficient to inhibit nuclease-induced polynucleotide degradation for at least 10 minutes, more typically for at least about 30 minutes, more typically for at least 60 minutes, more typically for at least 90 minutes, and even more typically for at least 120 minutes, as compared to unprotected polynucleotide. Lipid-conjugated polyamide compounds of the present invention are effective at inhibiting nuclease-induced polynucleotide degradation to the extent that lipid-conjugated polyamide-protected polynucleic acid typically exhibit less than about 80% of the degradation exhibited by unprotected (i.e., neat) polynucleotide) during the same time period, more typically less than about 50%, even more typically less than about 30%, and more typically, less than about 20%.

Compositions of lipid-conjugated polyamide compounds and polynucleic acid that are particularly effective at enhancing polynucleotide uptake by cells are those where the lipid-conjugated polyamide compound has formula (I), where W is $CH_2$, $R_a$ contains a lipid moiety (preferably a phosphatidylethanolamine), n is greater than 1, and each n-mer contains both cationic and neutral $R_1$ sidechain groups. This lipid-conjugated polyamide compound is also effective at protecting polynucleotides from nuclease-induced degradation.

Dilution-Concentration Method For Making Stable Polynucleic Acid/Delivery Vehicle Complex Preparations In still a further embodiment, the present invention provides a method of making a stable preparation of a polynucleic acid complexed with a delivery vehicle, said method comprising:
  a) combining a polynucleic acid with a first liquid carrier to form a dilute polynucleic acid solution that is substantially precipitant-free;
  b) combining a delivery vehicle-forming compound with a second liquid carrier to form a delivery vehicle solution that is substantially precipitant-free;
  c) combining said dilute polynucleic acid solution with said delivery vehicle solution to form a dilute preparation of delivery vehicle/polynucleic acid complex; then
  d) reducing the volume of said dilute preparation to form a stable preparation of delivery vehicle/polynucleic acid complex,
    wherein the concentration of polynucleic acid in said stable preparation is higher than the concentration of polynucleic acid in said dilute polynucleic acid solution, and
    wherein said stable preparation is substantially precipitant-free.

It has been discovered that when delivery vehicle/polynucleic acid complexes are formulated in liquid carrier in accordance with the "dilution-concentration" method of formulation, the resulting complexes are stable for relatively long periods of time with respect to particle size and transfection efficiency. In addition, the stable preparations are characteristically precipitant-free. Thus, unlike conventional delivery vehicle/polynucleic acid preparations in which equal volumes of dilute solutions of polynucleic acid and delivery vehicle are mixed together just prior to transfection, stable preparations made according to the invention dilution-concentration method of formulation can be prepared and stored up to days prior to transfection without substantial change in transfection efficiency. As used herein, the term "transfection efficiency" refers to the quantity or activity of protein expressed, or polynucleic acid synthesized, as a result of administration of a delivery vehicle/polynucletide complex to a cell.

Typically, the particle size distribution of delivery vehicle/polynucleotide complexes in the stable preparations changes by less than about 40% one day after formulation by the invention method, as compared to the particle size distribution of the complexes immediately after formulation. More typically, the particle size distribution of delivery vehicle/polynucleotide complexes in the stable preparations changes by less than about 30%, more typically by less than about 20%, and even more typically by less than about 15%, one day after formulation according to the concentration method of the present invention, as compared to the particle size distribution of the complexes immediately after formulation.

More typically, the particle size distribution of the delivery vehicle/polynucleotide complexes in the stable preparations changes by less than about 40%, even more typically less than about 30%, usually less than 20%, and more usually less than about 15%, five to eight days after formulation by the invention method, as compared to the particle size distribution of the complexes immediately after formulation.

As used herein, the term "dilute polynucleic acid solution" refers to a solution having a concentration of less than about 300 µg polynucleic acid/ml. Typically, dilute polynucleic acid solutions have polynucleic acid concentrations of less than about 250 µg/ml, more typically less than about 150 µg/ml, and even more typically less than about 100 µg/ml. Preferably, dilute polynucleic acid solutions have polynucleic acid concentrations of less than about 50 µg/ml.

The concentration of polynucleic acid in stable preparations of delivery vehicle/polynucleic complex is greater than the polynucleic acid concentration of the dilute polynucleic acid solution, and is typically at least about 150 µg (polynucleotide)/ml (preparation). More typically, the concentration of polynucleotide in stable preparation is at least about 250 µg/ml, more typically at least about 500 µg/ml, and even more typically at least about 1 mg/ml, and even more typically at least about 2 mg/ml The concentration of delivery vehicle-forming compound employed in the delivery vehicle solution will vary depending on the ratio of DNA to delivery vehicle desired and the solubility properties of the delivery-vehicle-forming compound employed. Those having ordinary skill in the art will recognize that the concentration and volume of delivery vehicle-forming compound in second liquid carrier can be adjusted to achieve the desired target ratio of delivery vehicle to DNA.

When the delivery vehicle-forming compound is a lipid-conjugated polyamide of the present invention, the concentration of the delivery vehicle solution is typically not more than about 5 mg/ml, more typically not more than about 2.5 mg/ml, and typically at least about 1.25 mg/ml. The volumes of delivery vehicle solution and dilute polynucleic acid solution combined are preferably selected such that the ratio of lipid-conjugated polyamide to polynucleic acid is about 5 mg lipid-conjugated polyamide to about 1 mg polynucleic acid. Thus, for example, if a 5 mg/ml lipid-conjugated polyamide solution is used as the delivery vehicle solution, combination with an equal volume of a 1 mg/ml polynucleic acid solution will yield a ratio of lipid-conjugated polyamide to polynucleic acid of 5 mg lipid-conjugated polyamide to 5 mg polynucleic acid.

The first liquid carrier may be the same or different from the second liquid carrier. Suitable first and second liquid carriers include the liquid carriers described herein. The term "delivery vehicle" used herein refers to an ordered structure that is capable of complexing with or enveloping a polynucleotide. Suitable delivery vehicles include liposomes, micelles, vesicles, and the like. As used herein, the term "delivery vehicle-forming compound" refers to a compound that is capable of forming a delivery vehicle. Exemplary delivery vehicle-forming compounds include amphipathic lipids, non-lipid polycationic compounds, lipid-conjugated polyamide compounds, and the like.

After the dilute polynucleotide solution and delivery vehicle preparation are combined, the volume of the resulting mixture is reduced. Suitable methods for reducing the volume of the resulting mixture include, for example, centrifugal filtration, vacuum filtration, as well as other methods for volume reduction that are well known to those having ordinary skill in the art. Typically, the volume of the resulting mixture is reduced such that the concentration of polynucleotide in the preparation is greater than about 150 $\mu$g/ml. The final concentration of the concentrated preparation can be lowered after the volume reduction step by adding sufficient liquid carrier to the preparation to achieve the desired concentration.

As used herein, the term "precipitant-free" refers to a preparation or solution that is free of solid material, i.e., precipitant material, as visually detected by the naked eye.

It has been discovered that transfection of cells using stable delivery vehicle/polynucleotide complex preparations is typically more efficient than with complexes formed by the conventional method of mixing equal volumes of dilute solutions of polynucleotide and delivery vehicle together, immediately prior to transfection, as illustrated in FIG. 14.

The invention will now be described in greater detail with reference to the following non-limiting examples.

EXAMPLE 1

Preparation of Lipid-Conjugated Polyamide Compounds

Synthesis of Lipid-Conjugated Polyamide Compounds (1) Synthesis of Oligomer Reactant A fritted reaction vessel was charged with 100 mg of Fmoc-Rink amide resin with a substitution level of about 0.50 mmol/g resin. Two milliliters of dimethylformamide (DMF) as added to the resin. The mixture was agitated for 1–2 minutes to swell the resin, then the DMF was drained. The Fmoc groups were removed by adding 2.0 ml of 20% piperidine in DMF to the resin, then agitating for 1 minute. The solution was then drained from the resin. Another 2 ml of 20% piperidine in DMF was added to the resin, followed by agitation for 15 minutes, after which, the DMF was then drained from the resin.

The resin was washed by adding 2 ml of DMF to the resin, followed by agitation to form a uniform slurry. The resin slurry was agitated by bubbling argon up through the bottom of the fritted vessel. The DMF was removed from the resin by vacuum filtration through the fritted bottom of the reaction vessel until the resin appeared dry (typically about 5 seconds). The washing step was repeated 6 times with DMF.

The deblocked amine was then acylated by adding 850 $\mu$l of 1.2 M bromoactic acid in DMF to the resin, followed by 200 $\mu$l of N,N'-diisopropylcarbodiimide (DIC). This mixture was agitated for 45 minutes at 35° C., then the solution was drained from the resin. The resin was washed with 6×2 ml aliquots of DMF. Amine displacement was effected by treating the resin with 850 $\mu$l of a 1 M solution of an amine in dimethylsulfoxide (DMSO). This mixture was agitated at 35 ° C. for 20 minutes, then the amine solution was drained from the resin. After the amine displacement step, the resin was washed with 6×2 ml aliquots of DMF. This completed one cycle of acylation and displacement.

The second cycle was initiated by acylation using bromoacetic acid and DIC, followed by displacement with a second amine as described above. This acylation/displacement cycle was repeated until the desired oligomer was reached.

The N-terminus of the resulting oligomer was acylated at 35° C. for 45 minutes with 850 $\mu$l of bromoacetic acid in DMF (1.2 M) and 200 $\mu$l DIC.

(2) Displacement of Bromide from Bromoacetylated Oligomer Reactant with Dimyristoyl Phosphatidylethanolamine A quantity of 254 mg of dimyristoyl phosphatidylethanolamine (DMPE) (Genzyme, Cambridge, Mass.) was suspended in 2 ml of 15% methanol in chlorobenzene, then treated with 30 $\mu$L of 12.8 N aqueous KOH. The resulting solution of DMPE was added to the bromoacetylated oligomer on resin from (1), above, and the reaction was agitated by bubbling argon for 1 second every 30 seconds over a period of 14 hours at 35° C. Next, the resin was thoroughly washed with 15% methanol in chlorobenzene to remove unreacted DMPE.

The resulting lipid-conjugated polyamide compound was cleaved from the resin and deprotected using 95% TFA in water, then lyophilized to yield a crude product.

This method was repeated using dipalmitoyl phosphatidylethanolamine (DPPE) and dioleoyl phosphatidylethanolamine (DOPE). Lipid-conjugated polyamide compounds prepared in accordance with this method are show in Table 1 and Table 2 below.

TABLE 1

Lipid-Conjugated N-Substituted Polyglycine Compounds[†]

| Compound No. | n | m | $R_1$ | $R_4$ |
|---|---|---|---|---|
| 1 | 1 | 2 | 2-aminoethyl | tridecyl |
| 2 | 1 | 4 | 2-aminoethyl | tridecyl |
| 3 | 1 | 10 | 2-aminoethyl | tridecyl |
| 4 | 1 | 2 | 2-aminoethyl | pentadecyl |
| 5 | 1 | 4 | 2-aminoethyl | pentadecyl |

TABLE 1-continued

Lipid-Conjugated N-Substituted Polyglycine Compounds[†]

| Compound No. | n | m | $R_1$ | $R_4$ |
|---|---|---|---|---|
| 6 | 1 | 10 | 2-aminoethyl | tridecyl |
| 7 | 1 | 2 | 3-aminopropyl | tridecyl |
| 8 | 1 | 4 | 3-aminopropyl | tridecyl |
| 9 | 1 | 10 | 3-aminopropyl | tridecyl |
| 10 | 1 | 2 | 3-aminopropyl | pentadecyl |
| 11 | 1 | 4 | 3-aminopropyl | pentadecyl |
| 12 | 1 | 10 | 3-aminopropyl | pentadecyl |

[†]Compounds of formula (I) where W is $CH_2$, $R_c$ is $NH_2$, and $R_a$ is defined by formula (III), where p is 2.

TABLE 2

Examples of Lipid-Conjugated N-substituted Polyglycine Compounds Having Repeating Trimer Units[†]

| Compound No. | m | $R^1_1$ | $R^2_1$ and $R^3_1$ | $R_4$ |
|---|---|---|---|---|
| 13 | 3 | 2-aminoethyl | 2-phenylethyl | tridecyl |
| 14 | 3 | 2-aminoethyl | (S)-1-methylbenzyl | tridecyl |
| 15 | 2 | 2-aminoethyl | 2-(4'-methoxyphenyl)ethyl | tridecyl |
| 16 | 3 | 2-aminoethyl | 2-(4'-methoxyphenyl)ethyl | tridecyl |
| 17 | 4 | 2-aminoethyl | 2-(4'-methoxyphenyl)ethyl | tridecyl |
| 18 | 8 | 2-aminoethyl | 2-(4'-methoxyphenyl)ethyl | tridecyl |
| 19 | 12 | 2-aminoethyl | 2-(4'-methoxyphenyl)ethyl | tridecyl |
| 20 | 3 | 2-aminoethyl | 2-(4'-methoxyphenyl)ethyl | cis-8-heptadecyl |
| 21 | 3 | 2-aminoethyl | pentyl | tridecyl |
| 22 | 3 | 2-aminoethyl | pentyl | cis-8-heptadecyl |
| 23 | 3 | 2-aminoethyl | 3-methylbutyl | tridecyl |
| 24 | 3 | 2-aminoethyl | 3-methylbutyl | cis-8-heptadecyl |

[†]Compounds of formula (IV) where W is $CH_2$, $R_c$ is $NH_2$, and $R_a$ is defined by formula (III), where p is 2.

B. Characterization of Lipid-Conjugated Polyamide Compounds

The lyophilized crude product from part A was dissolved in 5 ml of 50% (v/v) acetonitrile in water, and resulting solution was applied to a Delta-Pak™ C4 column (15 μm 300 Å) equilibrated with 80% (v/v) solvent B (0.1% (v/v) TFA in acetonitrile) in solvent A (0.1% (v/v) TFA in water) on a Water Prep LC3000 system equipped with a UV detector (Waters Corp., Milford, Mass.). Peaks were eluted with a linear gradient of 80% (v/v) solvent B in solvent A to 100% solvent B over 20 minutes, followed by 100% solvent B for 15 minutes at a flow rate of 50 ml/min. Peaks were monitored at 220 nm. the fractions containing the desired lipid-conjugated polyamide compounds were combined and concentrated in vacuo.

Products were characterized by analytical reverse phase HPLC using a Vydac C4 column (5μm 300Å, 1.0×150 mm) on a MAGIC 2002 liquid chromatography system (Michrom BioResource, Auburn, Calif.) and electrospray ionization mass spectrometry (Micromass, FISONS Instruments, Bevely, Mass.).

Chromatography of the reaction products from part A(2) of this example generated large sharp peaks, which correspond to the lipid-conjugated polyamide compounds, and much smaller peaks, which correspond to unreacted oligomers. Mass spectroscopy confirmed the theoretical molecular weights of the synthesized lipid-conjugated polyamide compounds from part A(2) in this example. Thus, these results confirm the predicted molecular weights of the lipid-conjugated polyamide compounds.

EXAMPLE 2

Preparation of Lipid-Conjugated Polyamide Compounds Complexed with Plasmid DNA

Figure 2:
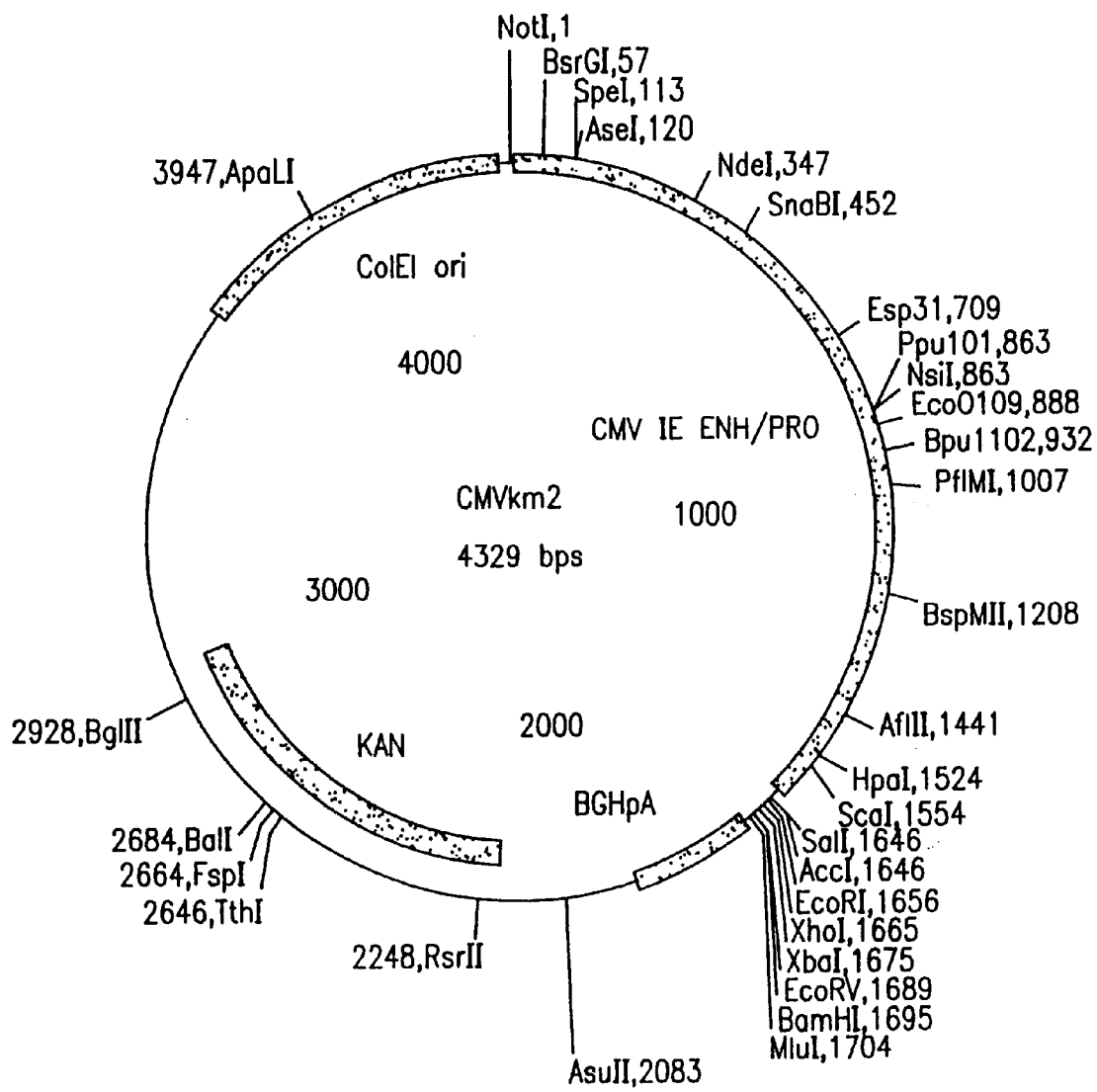
FIG. 2 is a plasmid map of vector CMVkm2.

Lipid-conjugated polyamides (from Example 1) complexed with plasmid DNA were prepared. The plasmid used in these experiments was pCMVkmLUC. Plasmid pCMVkmLUC was constructed by inserting the luc+ gene from pSP—luc+(Promega Corp. Madison, Wis.) into the expression vector pCMVkm2. The sequence of vector CMVkm2 is depicted in SEQ ID NO: 1. A plasmid map of vector CMVkm2 is shown in FIG. 2.

Briefly, pSP-luc+was digested with the restriction enzymes Nhe1-EcoRV (Boehringer Mannheim, Indianapolis, Ind.) and a fragment of 1691 bp was isolated by standard methods. This fragment was inserted into pCMVkm2, which had been digested with XbaI, EcoRV using the Rapid Ligation Kit (Boehringer Mannheim, Indianapolis, Ind.). The luc+gene was cloned into pCMVkm2 such that expression is driven by the CMV immediate early enhancer promoter and terminated by the bovine growth hormone polyadenylation signal.

Lipid-conjugated polyamide compounds synthesized in Example 1 were dissolved in sterile water at a concentration of 5 mM and sonicated for 1 minute to get a clear solution. A 5 mM solution of pCMVkmLUC in sterile water was prepared. Equal volumes of the lipid-conjugated polyamide compound solution and plasmid solution were mixed together and allowed to sit for 15 minutes at room temperature before transfection. For transfection studies, OptiMEM (GibcoBRL, Gaithersburg, Md.) was used instead of sterile water.

Complexes were also prepared by mixing lipid-conjugated polyamide compounds with DOPE or cholesterol in an equal molar ratio, then sonicated to form liposomes. Plasmid DNA was then added to these preformed liposomes to form complexes.

Complexes of Lipofectin® (GibcoBRL, Gaithersburg, Md.) and DMRIE-C™ (GibcoBRL, Gaithersburg, Md.) and plasmid DNA were also prepared as controls in the following examples, in accordance with manufacturer's directions.

EXAMPLE 3

Characterization of Lipid-Conjugated Polyamide Compounds Complexed with Plasmid DNA Rehydration of the lyophilized Compound 16 (see Table 2) in sterile water produced a clear solution which did not scatter light. Under negative-stain electron microscopy, the lipid-conjugated polyamide compound in this solution appeared as aggregates of most cylindrical micelles, with some spherical micelles with diameters of between about 10 to about 15 nm. While mixing a solution of Compound 16 with the pCMVkmLUC solution from Example 3, dynamic light scattering measurements (N4 Plus, Coulter Instruments, Miami, Fla.) indicated that particle sizes reached a minimum of about 120 nm when the +/− charge ratio was between about 2 and about 4. The particles sizes of these complexes increased slightly as the charge ratio changed. Negative-stain electron microscopy of a 2:1 +/− charge ratio complex indicated the formation of homogeneous, spherical particles with diameters of around 150 nm.

Dynamic light scattering measurements were similarly taken while mixing Compound 23 with pCMVkmLUC. The particle sizes of the resulting lipid-conjugated polyamide/DNA complex reached a minimum of 120 nm when the +/− charge ratio was between about 2 and about 4. When the charge ratio increased or decreased, the particle sizes of these complexes increased slightly.

Zeta potential measurements (Delsa 400, Coulter Instruments) indicated the zeta potential of the Compound 16/DNA complex increased steadily as the ratio of lipid-conjugated polyamide to DNA increased, and charge neutralization was realized at a charge ratio between about 0.5 and 1.

Complex formation was also characterized by agarose gel mobility shift assay. Complexes of Compound 16 with 1 $\mu$g pCMVkmLUC at a +/− charge ratio of 1 or above, were loaded onto a 1% agarose gel (70V, 1 hour) to examine the retardation of the complexed plasmid DNA, as compared to naked plasmid DNA. Gel mobility shift confirmed that the plasmid DNA was retained in the complex.

EXAMPLE 4

Characterization of DNA Stability in Complexes with Lipid-Conjugated Polyamide Compounds To determine whether lipid-conjugated polyamide compounds of the present invention inhibit degradation of complexed DNA by DNase 1 (Boehringer Mannheim, Indianapolis, Ind.), lipid-conjugated polyamide/DNA complexes were treated with DNase 1 and the results were analyzed by agarose gel electrophoresis. pCMVkmLUC (10 $\mu$g) and lipid-conjugated /pCMVkmLUC complexes containing 10 $\mu$g of pCMVkmLUC were incubated at 37° C. with 10 units of DNase 1 in 50 $\mu$l of 10 mM $MgCl_2$ for 15 minutes. An aliquot (1 $\mu$g DNA) of complex/DNase mixture was loaded (the loading buffer contained 1% SDS) onto a 1% agarose gel (70V, 1 hour) to examine the integrity of the plasmid DNA.

The results indicated that lipid-conjugated polyamide compounds having either aromatic or aliphatic $R_1$ groups were effective at providing resistance to DNase degradation, however, aromatic $R_1$ groups appeared to provide somewhat greater resistance to degradation. These results suggest that lipid-conjugated polyamide compounds having aromatic $R_1$ groups complex more strongly with DNA.

Furthermore, lipid-conjugated polyamide compounds of formula (IV), having the $R_1^1:R_1^2:R_1^3$ motif of aminoethyl:2-(4'-methoxyphenyl)ethyl:2-(4'-methoxyphenyl)ethyl, appeared to protect the plasmid DNA to a greater extent, than other motifs, as evidenced by the greater amount of supercoiled plasmid DNA retained. This result appeared to be independent of the length of the lipid-conjugated polyamide compound. Plasmid DNA stability was also evaluated as a function of complex +/− charge ratio. Lipitoid/polynucleotide complexes having different charge ratios were prepared by mixing different amounts of Compound 16 with a fixed amount of plasmid DNA. No significant degradation was observed with any of the charge ratios evaluated, i.e., +/− 10:1, 8:1, 4:1 and 2:1. However, supercoil conformation was maintained to a greater extent at higher charge ratios as compared to lower charge.

EXAMPLE 6

Transfection Method and Assay

Three cell lines were used in the transfection studies, HT1080 (American Type Culture Collection, Rockville, Md., Accession No. CCL 121), NIH3T3 (from culture collection stock of Chiron Corp., Emeryville, Calif.), and Cos6 M (from laboratory of E. Glazer, Chiron Corp. Emeryville, Calif.). Prior to transfection, the cells (2 ml of a suspension of $1\times10^5$ cells/ml DME-FCS) were plated into each well of a 6-well plate (Corning, Cambridge, Mass.) and moved gently to evenly disperse the cells. The cells were transfected 24 hours later.

For transfection, both transient and stable complexes containing plasmid (GibcoBRL, Gaithersburg, Md.). A transfection medium of complexed DNA was added to each well at 1 $\mu$g pCMVkmLUC/well, and at a concentration of 1 $\mu$g/100 $\mu$l . All tested conditions were performed in duplicate wells. Cells were cultured with transfection medium for 3 hours at 37° C. The transfection medium was removed by pipet without disturbing the cell layer and replaced with 2 ml of either DME-FCS (for serum-positive conditions) or OptiMEM (for serum-free conditions). The cells were reincubated for 48 hours, then the medium discarded. The cells were then rinsed twice with DPBS (JRH Biosciences, Lenexa, Kans.)

Reporter lysis buffer (300 $\mu$l/well) (Promega Corp., Madison, Wis.) was added to the wells and the cells were allowed to lyse for 15 to 20 minutes on a rocker. The cell lysate from each well was transferred to an eppendorf tube using a cell scraper (Fisher Scientific, Pittsburgh, Pa.), followed by a freeze (ethanol-dry ice)-thaw cycle and microfugation at maximum speed for 2 minutes.

Firefly luciferase activity for the lysates was assayed using the Luciferase Assay Kit (Promega Corp., Madison, Wis.) and an ML2250 automated luminometer (Dynatech, Chantilly, Va.) in accordance with manufacturer's directions.

EXAMPLE 7

Evaluation of Transfection Efficiency as a Function of Lipid-Conjugated Polyamide/DNA Complex Charge Density Lipid-conjugated polyamide/DNA complexes were prepared from Compound 16 and pCMVkmLUC in OptiMEM as described in Example 2, which had +/− charge densities of 0.5:1, 1:1, 2:1, 4:1, and 8:1. HT 1080 cells were transfected and assayed in accordance with the method described in Example 6. The relationship between transfection efficiency, i.e., luciferase activity, and complex charge density is shown in FIG. 2. The results indicate that transfection of HT1080 cells using Compound 16 was most efficient when the +/− charge density of the complex was about 2:1. The results also indicate that serum did not appear to have a significant influence on transfection efficiency.

EXAMPLE 8

Evaluation of the Effect of Oligomer Length on the Transfection Efficiency of Lipid-Conjugated Polyamide Compounds Lipid-conjugated polyamide/pCMVkmLUC complexes were prepared from Compounds 15–19, having a +/− charge ratio of 2: 1, in OptiMEM according to Example 2. Compounds 15–19 all have the same general structure, i.e. formula (IV), identical side chains and lipid groups, however, they differ with respect to oligomer length, i.e., the integer m is different for each of these compounds. The integer m is 2, 3, 4, 8, and 12, for Compounds 15, 16, 17, 18, and 19, respectively. HT1080 cells were transfected with complexes prepared from each of these compounds, then assayed as described in Example 6.

Figure 3:
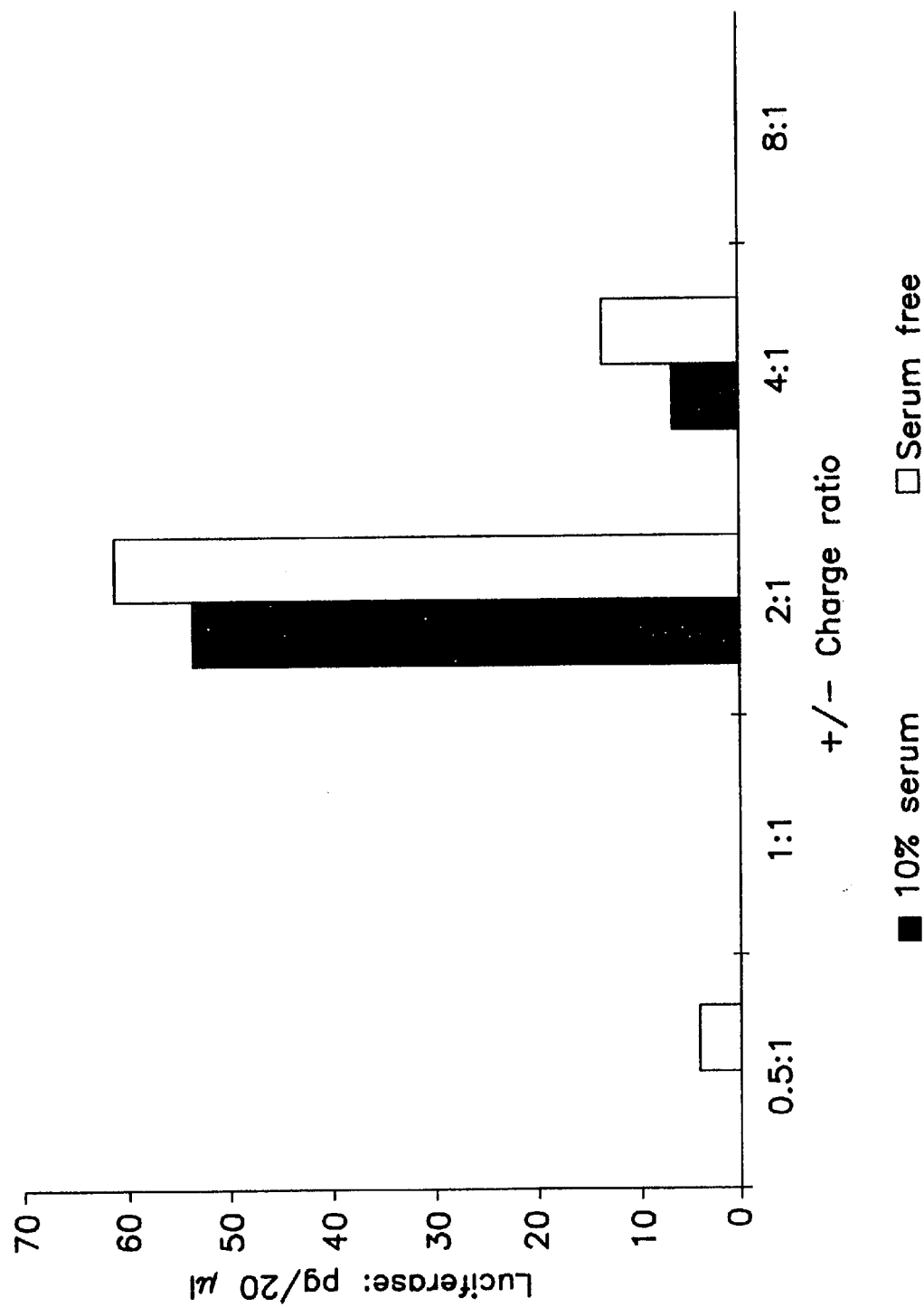
FIG. 3 shows the effect of the +/− charge ratio of a complex of plasmid DNA (pCMVkmLUC) and a lipid-conjugated polyamide of the present invention (i.e., Compound 16 from Table 2) on the transfection of HT1080 cells.

The results, shown in FIG. 3, indicate that for this particular series of compounds, transfection efficiency is highest for Compound 16 (m=3).

EXAMPLE 9

Effect of Lipid Moiety Type on Transfection Efficiency

Conjugated-lipid polyamide/pCMVkmLUC complexes were prepared from Compounds 16 and 23, both DMPE-conjugated compounds, and Compounds 20 and 24, both DOPE-conjugated compounds, having a +/− charge density ratio of 2: 1, as described in Example 2. HT1080 cells were transfected using these complexes and transfection efficiency was assayed, both in accordance with the methods described in Example 6

The results, shown in FIG. 4, indicated higher transfection efficiencies for the DMPE-conjugated compounds, as compared to the DOPE-conjugated compounds.

EXAMPLE 10

Transfection of Different Cell Lines Using Livid-Conjugated Polyamide Compounds Lipid-conjugated polyamide/pCMVkmLUC plasmid complexes were prepared from Compounds 16 and 23 in OptiMEM, having a +/− charge density ratio of 2:1, according to Example 2. In addition, Lipofectin/pCMVkmLUC and DMRIE-C™/pCMVkmLUC complexes were prepared according to manufacturer's directions in OptiMEM. HT1080, Cos6M, and NIH3T3 cells were transfected with the complexes, and subsequently assayed for luciferase activity according to Example 6.

The results are shown in Table 3. These results demonstrate the higher transfection efficiencies of lipid-conjugated polyamide compounds, as compared to commercially available transfection preparations.

TABLE 3

Transfection Efficiency[†] of Lipid-Conjugated Polyamide Compounds

| | Transfection Vehicle | | | |
|---|---|---|---|---|
| Cell Line | Lipofectin ® | DMRIE-C ™ | Compound 16 | Compound 23 |
| HT1080 | 1/1[a] | 5.2/3[a] | 10/7[a] | 17.6/12.8[a] |
| COS6M | 1/1[a] | 8/27[a] | /26[a] | 3/29[a] |
| NIH3T3 | | 1/1[b] | 100/33[b] | 0.76/4.9[b] |

[†]Normalized Luciferase Activity (optiMEM, serum-free)/Normalize Luciferase Activity (serum)
[a]Both serum and serum-free activities are normalized to the corresponding luciferase activities from Lipofectin ®-mediated transfection.
[b]Both serum and serum-free activities are normalized to the corresponding luciferase activities from DMRIE-C™-mediated transfection.

EXAMPLE 11

Transfection of HT1080 Cells Using Various Lipid-Conjugated Polyamide Compounds Lipid-conjugated polyamide/pCMVkmLUC plasmid complexes were prepared from some of the lipid-conjugated polyamide compounds from Example 1, in OptiMEM as described in Example 2. The complexes had a +/− charge density ratio of 2:1 In addition, Lipofectin®/pCMVkmLUC and DMRIE-C™/pCMVkmLUC complexes were prepared according to manufacturer's directions in OptiMEM. HT1080 cells were transfected with the complexes, and subsequently assayed for luciferase activity according to Example 6.

The results are shown in below in Table 4.

TABLE 4

Transfection Efficiency[†a] of Lipid-Conjugated Polyamide Compounds

| Transfection Vehicle | Transfection Efficiency |
|---|---|
| Lipofectin ® | 1/1 |
| DMRIE-C ™ | 5.2/3 |
| Compound 2 | 2/0.2 |
| Compound 3 | 1.6/1.3 |
| Compound 8 | 0.1/0.1 |
| Compound 9 | 0.1/0.1 |
| Compound 13 | 4.3/3.2 |
| Compound 14 | 5.7/4 |
| Compound 15 | 4.1/2.4 |
| Compound 16 | 10/7 |
| Compound 17 | 1.7/1.1 |
| Compound 20 | 4/3 |
| Compound 21 | 6/9.3 |
| Compound 22 | 3.5/6.2 |
| Compound 23 | 17/12 |
| Compound 24 | 2/7.2 |

[†]Normalized Luciferase Activity (optiMEM, serum-free)/Normalize Luciferase Activity (serum)
[a]All activities were normalized to the corresponding serum and serum-free luciferase activities from Lipofectin ®-mediated transfection.

Lipid-conjugated polyamide compounds having repeating n-mer units with both cationic and neutral sidechains (RI) were generally more effective at mediating transfection as compared to lipid-conjugated polyamide compounds having only cationic sidechains.

EXAMPLE 12

In vivo Transfection Using a Lipid-Conjugated Polyamide Compound/pCMVkmLUC Complex A preparation of lipid-conjugated polyamide/pCMVkmLUC complex was prepared by mixing an 200 μl of a solution of 60 μg of pCMVkmLUC in 200 μl of D5W (5% dextrose) with 200 μl of 2.9 mg of Compound 16 in 200 pl of D5W (5% dextrose), such that the complex +/− charge ratio was 8:1. The final volume of the lipid-conjugated polyamide/DNA complex preparation was 400 μl . A 400 μl dosage of the preparation was injected into the tail vein of a Balb/C mouse.

The mouse was sacrificed 24 hours post-injection and the lungs, liver, heart, kidney, and spleen were harvested. The harvested organs were placed in 2.0 ml screwcap tubes in which one third of the volume of the tubes was filled with glass beads (BioSpec Products, Inc., Bartlesville, Okla.) Please provide source location. The tubes were frozen in liquid nitrogen, then stored at −70° C.

To extract luciferase from the harvested organs, a 300 μl aliquot of 1×Reporter Lysis Buffer (Promega Corp., Madison, Wis.) was added to each tube. The contents of the tubes were then homogenized for 1 minute at 4° C. After adding a 200 μl aliquot of 1×RLB to each tube, the tube contents were vortexed for 30 minutes in the cold room. The tubes and their contents were then frozen in an ethanol/dry ice bath, then thawed in a water bath at 20° C., for three cycles. The tubes were then centrifuged at 12,500 rpm for 5 minutes in a cold room. After centrifugation, the supernatant was collected by pipet.

The supernatant was assayed for luciferase activity using the Promega Luciferase assay system and the Dynatech ML2250 automated luminometer (Dynatech, Chantilly, Va.) in accordance with the manufacturer's directions.

The results, shown in FIG. 5, indicate that luciferase is expressed in mouse lung, liver, and, to a lesser extent, spleen tissue. These results demonstrate the efficacy of lipid-conjugated polyamide compounds at mediating in vivo transfection.

EXAMPLE 13

Dilution-Concentration Method for Formulating Stable Preparations of Delivery Vehicle/ Polynucleotide Complexes I. Charge Calculations The concentration of negative charges on DNA was calculated as 3.03 nmol of phosphate per 1 µg of DNA based on an average molecular weight of 330 daltons for each nucleotide. The formula weight of each lipid-conjugated polyamide compound was calculated as semi-trifluoroacetate salt (50% of amino groups form salt with TFA), and the concentration of the lipid-conjugated polyamide compound was determined on the basis of the basis of the lyophilized product from Example 1.

II. Complex Formation

All steps were conducted at ambient temperature. Diagnosis grade purified water (DGPW) was used to prepare all stock solutions. Lipid-conjugated polyamide/pCMVkmLUC complexes were prepared having +/− charge ratios of 0.5:1, 1:1, 2:1, 4:1, and 8:1. A dilute solution of 50 µg/ml polynucleotide in was prepared, corresponding to 151 82 M of negative charge. A 5mM solutions of lipid-conjugated polyamide Compound 16 was prepared.

A volume of the DNA solution was quickly added to an equal volume of each lipid-conjugated polyamide solution with gentle agitation. It was observed that slow addition of the two solutions tended to result in the formation of larger complexes and occasional precipitates. Better results were achieved when the DNA solution was added to the lipid-conjugated polyamide solution rather than vice-versa.

The formulations were concentrated using commercially available ultrafiltration membrane concentrator devices with appropriate nominal molecular weight cutoff (e.g., 100 kd). Two milliliters of each dilute lipid-conjugated polyamide/pCMVkmLUC complex preparation (in 30% (v/v) ethanol) were placed in a Centricon®-100 (Amicon Inc., Beverly, Mass.) and centrifuged at 1000×g for 30 minutes or until the volume of the retentate contained the complex was approximately 50 µl . The filtrate was removed from the bottom receiver. The retentate was diluted with 2 ml of 5% glucose, and concentrated to 50 µl again by repeating the above procedure. This operation was repeated again to make a concentrated, stable preparation containing 1 mg/ml of pCMVkmLUC in 5% glucose. The method can be conducted cold (e.g., at 4° C.) or at ambient temperatures. Generally, the final concentration of DNA in the retentate can be as high as 1 mg/ml without any visible precipitation.

Zeta potential measurements were taken of each concentrated preparation at day 1, day 2, and day 8 post-formulation. The results, shown in FIGS. 6 and 7, indicate that the zeta potential of the complexes in the concentrated preparation remained substantially stable over a period of 8 days.

Dynamic light scattering measurements (N4 Plus, Coulter Instruments, Miami, Fla.) were taken for each concentrated preparation of lipid-conjugated polyamide/pCMVkmLUC complex. The results, shown in FIGS. 8 and 9, indicate that the particle sizes of the complexes also remained substantially stable over a period of 8 days.

HT1080 cells were transfected with each concentrated preparation of lipid-conjugated/pCMVkmLUC complex at 2- and 18-days post-formulation (Compound 16) and at 4- and 12-days post-formulation, according to the method described in Example 6. A preparation of DMRIE-C™/pCMVkmLUC complexes was prepared using conventional methods described in Example 2, and HT1080 cells were transfected. Cell confluence was also measured using a microscope and estimating the percentage of live cells.

The results, shown in FIGS. 10–12 indicated that luciferase activity in cells transfected with lipid-conjugated polyamide/pCMVkmLUC complexes prepared according to the "concentration" formulation method, was higher than for DMRIE-C™/pCMVkmLUC complexes prepared according to conventional methods. The results indicate that cell confluence is high for the 0.5:1, 1:1, and 2:1 +/− charge ratio complexes and the DMRIE-C™, and lower for the 4:1 and 8:1+/− charge ratio complexes. Doubling the amount of transfection preparation increased luciferase expression in complexes having a 2:1 +/− charge ratio, but decreased expression in complexes having a 4:1 +/− charge ratio, as shown in FIG. 14. FIG. 14 also shows that cell confluence also decreased when the amount of 4:1 +/1 charge ratio complex was doubled.

The effect of using the conventional method for preparing delivery vehicle/DNA complexes, as described in Example 2, was compared to use of the concentration method for preparing delivery vehicle/DNA complex. Lipid-conjugated polyamide compounds (16 and 23)/pCMVkmLUC complexes were prepared according to the conventional method described in Example 2. HT1080 cells were transfected within 30 minutes of formulation. The results are designated "Mixing" in FIG. 15. Similarly, lipid-conjugated polyamide compound (16 and 23)/pCMVkmLUC complexes were prepared according to the concentration method followed by transfection of HT1080 cells 1 to 7 days post-formulation. The results are designated "Preformed" in FIGS. 14 and 15. Complexes of Lipofectin and DMRIE-C with pCMVkmLUC were also prepared using the conventional formulation method described in Example 2. The results, shown in FIG. 15, indicate that luciferase activity was higher in cells transfected with complexes formed by the concentration method, than in cells transfected with complexes formed by the conventional method. Cell viability was measured by staining with tryphan blue.

While the invention has been described in detail with reference to certain preferred embodiments thereof, it will be understood that modifications and variations are within the spirit and scope of that which is described and claimed.

What is claimed:

1. A method of making a stable preparation of a polynucleic acid complexed with a delivery vehicle, said method comprising:
 a) providing a polynucleic acid in a first liquid carrier as a dilute polynucleic acid solution that is substantially precipitant-free;
 b) providing a delivery vehicle-forming compound in a second liquid carrier as a delivery vehicle solution that is substantially precipitant-free;
 c) combining said dilute polynucleic acid solution with said delivery vehicle solution to form a dilute preparation of delivery vehicle/polynucleic acid complex; and
 d) reducing the volume of said dilute preparation to form a stable preparation of delivery vehicle/polynucleic acid complex, wherein the concentration of polynucleic acid in said stable preparation is higher than the concentration of polynucleic acid in said dilute polynucleic acid solution, and wherein said stable preparation is substantially precipitant-free,
 and wherein said delivery vehicle-forming compound is selected from (i) a lipid, selected from the group consisting of a phosphoglyceride, a glycosylglyceride, a sphingolipid, and a sterol, (ii) a polycationic non-lipid compound, and (iii) a lipid-conjugated polyamide compound comprising a repeating trimer of monomeric subunits and having the formula:

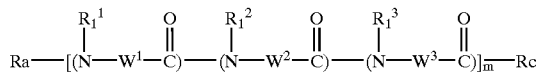

where
 m is an integer selected from 2 to about 48,
 Ra is selected from the group consisting of —OH, —H, —SH, —COOH, sulfonyl, a C1–C8 aliphatic group or a C3–C12 aryl, arylalkyl, arylalkenyl, or arylalkynyl group, any of which may include at least one heteroatom selected from the group consisting of nitrogen, sulfur, oxygen, and phosphorus; and a lipid moiety, wherein said lipid moiety may be conjugated to a linker moiety;
 each $R_1$ is independently selected from the group consisting of hydrogen, a C1–C8 aliphatic group or a C3–C12 aryl, arylalkyl, arylalkenyl, or arylalkynyl group, any of which may include at least one heteroatom selected from the group consisting of nitrogen, sulfur, oxygen, and phosphorus; and a lipid moiety, wherein said lipid moiety may be conjugated to a linker moiety, wherein at least one group $R_1$ is not hydrogen;
 Rc is selected froth the group consisting of —OH, —H, —SH, —NH$_2$, sulfonyl, hydrazine, a C1–C8 aliphatic group or a C3–C12 aryl, arylalkyl, arylalkenyl, or arylalkynyl group, any of which may include at least one heteroatom selected from the group consisting of nitrogen, sulfur, oxygen, and phosphorus; and a lipid moiety, wherein said lipid moiety may be conjugated to a linker moiety;
 and —each group W is selected from the group consisting of —CH$_2$CH$_2$—, CH$_2$-phenyl-, CH$_2$CH$_2$O, —CH$_2$CH=CH—, and —CR$_2$R$_3$—, where $R_2$ and $R_3$ are independently selected from the group consisting of hydrogen, a C1–C8 aliphatic group or a C3–C12 aryl, arylalkyl, arylalkenyl, or arylalkynyl group, any of which may include at least one heteroatom selected from the group consisting of nitrogen, sulfur, oxygen, and phosphorus; and a lipid moiety, wherein said lipid moiety may be conjugated to a linker moiety;
 wherein any said aryl, arylalkyl, arylalkenyl, or arylalkynyl group having fewer than 5 carbon atoms further includes at least one heteroatom;
 and wherein at least one of said groups Ra, Rc, $R_1$ for a single monomeric subunit, and W for a single monomeric subunit, comprises a lipid moiety.

2. The method according to claim 1 wherein said delivery vehicle is a liposome.

3. The method of claim 1, wherein at least one group $R_1$ is a cationic sidechain selected from the group consisting of aminoalkyl, (S)α-methylethylenediamino, trimethylaminoethyl, guanidinoalkyl, aminobenzyl, pyridinium, cationic sidechains found on naturally occurring amino acids, and derivatives thereof.

4. The method of claim 1, wherein at least one group $R_1$ is a neutral sidechain selected from the group consisting of (S)-α-methylbenzyl, (R)-α-methylbenzyl, benzyl, phenethyl, naphthylmethyl, (S)-α-methylnaphthyl, (R)-α-methylnaphthyl, N-propylpyrrolidinone, cyclohexylmethyl, furfuryl, 3,4,5-trimethoxybenzyl, alkoxyalkyl, isoamyl, p-methoxyphenethyl, neutral sidechains found on naturally occurring amino acids, aid derivatives thereof.

5. The method of claim 1, wherein at least one group $R_1$ is an anionic side chain selected from the group consisting of carboxy, carboxy methyl, carboxy ethyl, benzoic acid, phosphates, sulfates, and derivatives thereof.

6. The method of claim 1, where each group W is —CR$_2$R$_3$—.

7. The method of claim 6, where $R_2$ and $R_3$ are hydrogen.

8. The method of claim 7, wherein $R_a$ is selected from the group consisting of —OH, —H, —SH, —COOH, sulfonyl, and a lipid moiety, wherein said lipid moiety may be conjugated to a linker moiety.

9. The method of claim 7, wherein Rc is selected from the group consisting of —OH, —H, —SH, —NH$_2$, sulfonyl, hydrazine, and a lipid moiety, wherein said lipid moiety may be conjugated to a linker moiety.

10. The method of claim 7, wherein Rc is a lipid moiety, which may be conjugated to a linker moiety.

11. The method of claim 10, wherein said lipid moiety is a sterol.

12. The method of claim 7, wherein Ra is a lipid moiety, which may be conjugated to a linker moiety.

13. The method of claim 12, wherein said lipid moiety is a phosphatidyl ethanolamine or a phosphatidyl propanolamine, having a phosphoglyceryl head group comprising two alkyl or alkenyl moieties having from 6 to about 25 carbon atoms.

14. The method of claim 12, wherein said lipid moiety is a sterol.

15. The method of claims 14, wherein said sterol is a cholesterol.

16. The method of claim 15, wherein $R_1^1$ is a cationic sidechain, and $R_1^2$ and $R_1^3$ are neutral sidechains.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
       (A) LENGTH: 4328 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

```
GCCGCGGAAT TCGACTCTA  GGCCATTGCA TACGTTGTAT CTATATCATA ATATGTACAT       60
TTATATTGGC TCATGTCCAA TATGACCGCC ATGTTGACAT TGATTATTGA CTAGTTATTA      120
ATAGTAATCA ATTACGGGGT CATTAGTTCA TAGCCCATAT ATGGAGTTCC GCGTTACATA      180
ACTTACGGTA AATGGCCCGC CTGGCTGACC GCCCAACGAC CCCCGCCCAT TGACGTCAAT      240
AATGACGTAT GTTCCCATAG TAACGCCAAT AGGGACTTTC CATTGACGTC AATGGGTGGA      300
GTATTTACGG TAAACTGCCC ACTTGGCAGT ACATCAAGTG TATCATATGC CAAGTCCGCC      360
CCCTATTGAC GTCAATGACG GTAAATGGCC CGCCTGGCAT TATGCCCAGT ACATGACCTT      420
ACGGGACTTT CCTACTTGGC AGTACATCTA CGTATTAGTC ATCGCTATTA CCATGGTGAT      480
GCGGTTTTGG CAGTACACCA ATGGGCGTGG ATAGCGGTTT GACTCACGGG GATTTCCAAG      540
TCTCCACCCC ATTGACGTCA ATGGGAGTTT GTTTTGGCAC CAAAATCAAC GGGACTTTCC      600
AAAATGTCGT AATAACCCCG CCCCGTTGAC GCAAATGGGC GGTAGGCGTG TACGGTGGGA      660
GGTCTATATA AGCAGAGCTC GTTTAGTGAA CCGTCAGATC GCCTGGAGAC GCCATCCACG      720
CTGTTTTGAC CTCCATAGAA GACACCGGGA CCGATCCAGC CTCCGCGGCC GGGAACGGTG      780
CATTGGAACG CGGATTCCCC GTGCCAAGAG TGACGTAAGT ACCGCCTATA GACTCTATAG      840
GCACACCCCT TTGGCTCTTA TGCATGCTAT ACTGTTTTTG GCTTGGGGCC TATACACCCC      900
CGCTCCTTAT GCTATAGGTG ATGGTATAGC TTAGCCTATA GGTGTGGGTT ATTGACCATT      960
ATTGACCACT CCCCTATTGG TGACGATACT TTCCATTACT AATCCATAAC ATGGCTCTTT     1020
GCCACAACTA TCTCTATTGG CTATATGCCA ATACTCTGTC CTTCAGAGAC TGACACGGAC     1080
TCTGTATTTT TACAGGATGG GGTCCATTTA TTATTTACAA ATTCACATAT ACAACAACGC     1140
CGTCCCCCGT GCCCGCAGTT TTTATTAAAC ATAGCGTGGG ATCTCCGACA TCTCGGGTAC     1200
GTGTTCCGGA CATGGGCTCT TCTCCGGTAG CGGCGGAGCT TCCACATCCG AGCCCTGGTC     1260
CCATCCGTCC AGCGGCTCAT GGTCGCTCGG CAGCTCCTTG CTCCTAACAG TGGAGGCCAG     1320
ACTTAGGCAC AGCACAATGC CCACCACCAC CAGTGTGCCG CACAAGGCCG TGGCGGTAGG     1380
GTATGTGTCT GAAAATGAGC TCGGAGATTG GGCTCGCACC TGGACGCAGA TGGAAGACTT     1440
AAGGCAGCGG CAGAAGAAGA TGCAGGCAGC TGAGTTGTTG TATTCTGATA AGAGTCAGAG     1500
GTAACTCCCG TTGCGGTGCT GTTAACGGTG GAGGGCAGTG TAGTCTGAGC AGTACTCGTT     1560
GCTGCCGCGC GCGCCACCAG ACATAATAGC TGACAGACTA ACAGACTGTT CCTTTCCATG     1620
GGTCTTTTCT GCAGTCACCG TCGTCGACCT AAGAATTCAG ACTCGAGCAA GTCTAGAAAG     1680
CCATGGATAT CGGATCCACT ACGCGTTAGA GCTCGCTGAT CAGCCTCGAC TGTGCCTTCT     1740
AGTTGCCAGC CATCTGTTGT TTGCCCCTCC CCCGTGCCTT CCTTGACCCT GGAAGGTGCC     1800
```

```
ACTCCCACTG TCCTTTCCTA ATAAAATGAG GAAATTGCAT CGCATTGTCT GAGTAGGTGT   1860

CATTCTATTC TGGGGGGTGG GGTGGGGCAG GACAGCAAGG GGGAGGATTG GGAAGACAAT   1920

AGCAGGGGGG TGGGCGAAGA ACTCCAGCAT GAGATCCCCG CGCTGGAGGA TCATCCAGCC   1980

GGCGTCCCGG AAAACGATTC CGAAGCCCAA CCTTTCATAG AAGGCGGCGG TGGAATCGAA   2040

ATCTCGTGAT GGCAGGTTGG GCGTCGCTTG GTCGGTCATT TCGAACCCCA GAGTCCCGCT   2100

CAGAAGAACT CGTCAAGAAG GCGATAGAAG GCGATGCGCT GCGAATCGGG AGCGGCGATA   2160

CCGTAAAGCA CGAGGAAGCG GTCAGCCCAT TCGCCGCCAA GCTCTTCAGC AATATCACGG   2220

GTAGCCAACG CTATGTCCTG ATAGCGGTCC GCCACACCCA GCCGGCCACA GTCGATGAAT   2280

CCAGAAAAGC GGCCATTTTC CACCATGATA TTCGGCAAGC AGGCATCGCC ATGGGTCACG   2340

ACGAGATCCT CGCCGTCGGG CATGCGCGCC TTGAGCCTGG CGAACAGTTC GGCTGGCGCG   2400

AGCCCCTGAT GCTCTTCGTC CAGATCATCC TGATCGACAA GACCGGCTTC CATCCGAGTA   2460

CGTGCTCGCT CGATGCGATG TTTCGCTTGG TGGTCGAATG GGCAGGTAGC CGGATCAAGC   2520

GTATGCAGCC GCCGCATTGC ATCAGCCATG ATGGATACTT TCTCGGCAGG AGCAAGGTGA   2580

GATGACAGGA GATCCTGCCC CGGCACTTCG CCCAATAGCA GCCAGTCCCT TCCCGCTTCA   2640

GTGACAACGT CGAGCACAGC TGCGCAAGGA ACGCCCGTCG TGGCCAGCCA CGATAGCCGC   2700

GCTGCCTCGT CCTGCAGTTC ATTCAGGGCA CCGGACAGGT CGGTCTTGAC AAAAAGAACC   2760

GGGCGCCCCT GCGCTGACAG CCGGAACACG GCGGCATCAG AGCAGCCGAT TGTCTGTTGT   2820

GCCCAGTCAT AGCCGAATAG CCTCTCCACC CAAGCGGCCG GAGAACCTGC GTGCAATCCA   2880

TCTTGTTCAA TCATGCGAAA CGATCCTCAT CCTGTCTCTT GATCAGATCT TGATCCCCTG   2940

CGCCATCAGA TCCTTGGCGG CAAGAAAGCC ATCCAGTTTA CTTTGCAGGG CTTCCCAACC   3000

TTACCAGAGG GCGCCCCAGC TGGCAATTCC GGTTCGCTTG CTGTCCATAA AACCGCCCAG   3060

TCTAGCTATC GCCATGTAAG CCCACTGCAA GCTACCTGCT TTCTCTTTGC GCTTGCGTTT   3120

TCCCTTGTCC AGATAGCCCA GTAGCTGACA TTCATCCGGG GTCAGCACCG TTTCTGCGGA   3180

CTGGCTTTCT ACGTGTTCCG CTTCCTTTAG CAGCCCTTGC GCCCTGAGTG CTTGCGGCAG   3240

CGTGAAGCTG TCAATTCCGC GTTAAATTTT TGTTAAATCA GCTCATTTTT TAACCAATAG   3300

GCCGAAATCG GCAAAATCCC TTATAAATCA AAAGAATAGC CCGAGATAGG GTTGAGTGTT   3360

GTTCCAGTTT GGAACAAGAG TCCACTATTA AGAACGTGG ACTCCAACGT CAAAGGGCGA   3420

AAAACCGTCT ATCAGGGCGA TGGCGGATCA GCTTATGCGG TGTGAAATAC CGCACAGATG   3480

CGTAAGGAGA AAATACCGCA TCAGGCGCTC TTCCGCTTCC TCGCTCACTG ACTCGCTGCG   3540

CTCGGTCGTT CGGCTGCGGC GAGCGGTATC AGCTCACTCA AAGGCGGTAA TACGGTTATC   3600

CACAGAATCA GGGGATAACG CAGGAAAGAA CATGTGAGCA AAAGGCCAGC AAAAGGCCAG   3660

GAACCGTAAA AAGGCCGCGT TGCTGGCGTT TTTCCATAGG CTCCGCCCCC CTGACGAGCA   3720

TCACAAAAAT CGACGCTCAA GTCAGAGGTG GCGAAACCCG ACAGGACTAT AAAGATACCA   3780

GGCGTTTCCC CCTGGAAGCT CCCTCGTGCG CTCTCCTGTT CCGACCCTGC CGCTTACCGG   3840

ATACCTGTCC GCCTTTCTCC CTTCGGGAAG CGTGGCGCTT TCTCATAGCT CACGCTGTAG   3900

GTATCTCAGT TCGGTGTAGG TCGTTCGCTC CAAGCTGGGC TGTGTGCACG AACCCCCCGT   3960

TCAGCCCGAC CGCTGCGCCT TATCCGGTAA CTATCGTCTT GAGTCCAACC CGGTAAGACA   4020

CGACTTATCG CCACTGGCAG CAGCCACTGG TAACAGGATT AGCAGAGCGA GGTATGTAGG   4080

CGGTGCTACA GAGTTCTTGA AGTGGTGGCC TAACTACGGC TACACTAGAA GGACAGTATT   4140
```

```
                                               -continued

TGGTATCTGC GCTCTGCTGA AGCCAGTTAC CTTCGGAAAA AGAGTTGGTA GCTCTTGATC     4200

CGGCAAACAA ACCACCGCTG GTAGCGGCGG TTTTTTGTTT GCAAGCAGCA GATTACGCGC     4260

AGAAAAAAAG GATCTCAAGA AGATCCTTTG ATCTTTTCTA CTGAACGGTG ATCCCCACCG     4320

GAATTGCG                                                             4328
```